United States Patent [19]

Dunski et al.

[11] Patent Number: 4,806,675

[45] Date of Patent: Feb. 21, 1989

[54] METHOD OF MAKING MIXED PENTAERYTHRITOL ESTERS HAVING UP TO 75 PERCENT THIO-CONTAINING SIDE CHAINS

[75] Inventors: Neil Dunski, Creve Coeur; Ali A. Bazzi, Chesterfield, both of Mo.

[73] Assignee: Mallinckrodt, Inc., St. Louis, Mo.

[21] Appl. No.: 111,470

[22] Filed: Oct. 19, 1987

Related U.S. Application Data

[63] Continuation of Ser. No. 871,007, Jun. 5, 1986, Pat. No. 4,734,519.

[51] Int. Cl.$^4$ .......................................... C07C 149/20
[52] U.S. Cl. ....................................... 560/75; 560/59; 524/289
[58] Field of Search ................................. 560/59, 75

[56] References Cited

U.S. PATENT DOCUMENTS 3,275,597  9/1966  Mauz et al. .................... 528/289
3,758,549  9/1973  Dexter et al. .................. 528/289

FOREIGN PATENT DOCUMENTS 221343A  4/1985  Japan ........................... 560/59

*Primary Examiner*—Harold D. Anderson
*Assistant Examiner*—Frederick Krass
*Attorney, Agent, or Firm*—L. N. Goodwin; Roy J. Klostermann; Veo Peoples, Jr.

[57] ABSTRACT

Pentaerythritol co-esters derived from pentaerythritol, (3-alkyl-4-hydroxyphenyl)-alkanoic acids and alkylthioalkanoic acids or lower alkyl esters of such acids are useful as stabilizers of organic material normally susceptible to oxidative and/or thermal deterioration. The co-esters are advantageously prepared by transesterification of such esters with pentaerythritol. Preferred co-esters are (I) pentaerythritol tris[3,5-di-tert-butyl-4-hydroxyphenyl)propionate]-mono[3-n-dodecylthiopropionate] and (II) pentaerythritol bis[-(3,5-di-tert-butyl-4-hydroxyphenyl)propionate]-bis[3-n-dodecylthiopropionate]. The co-esters are especially useful in stabilizing applications for which physical mixtures of (i) (3-alkyl-4-hydroxyphenylalkanoic acid esters of polyols with (ii) polyalkanol esters of alkylthioalkanoic acids have heretofore been proposed.

13 Claims, No Drawings

METHOD OF MAKING MIXED PENTAERYTHRITOL ESTERS HAVING UP TO 75 PERCENT THIO-CONTAINING SIDE CHAINS

This is a continuation of application Ser. No. 871,007 filed June 5, 1986, now U.S. Pat. No. 4,734,519.

This invention relates to pentaerythritol co-esters useful in the stabilization of organic materials normally susceptible to oxidative and/or thermal deterioration, mixtures of the co-esters and organic material stabilized with the co-esters or mixtures thereof.

Numerous compounds, including various sterically hindered phenol derivatives, have been proposed for stabilizing organic materials, such as organic polymers, against oxidative and/or thermal degradation.

U.S. Pat. No. 3,644,482 (Dexter, Spivack and Steinberg), which issued on application Ser. No. 861,475 filed Sept. 26, 1969, discloses mono- and dialkylhydroxyphenyl alkanoic acid esters of alkane polyols. According to the patent the esters are stabilizers of organic material normally subject to oxidative deterioration as by light and/or heat. Among the synthetic organic polymeric substances set forth in the patent as materials "thus stabilized" are poly-alpha-olefins such as polyethylene, polypropylene, polybutylene, and the like, including copolymers of poly-alpha-olefins; polyisoprene; polybutadiene; polystyrene and copolymers such as those of high impact polystyrene containing copolymers of butadiene and styrene. Products obtained by the methods set forth in the patent for preparing the ester compounds are described as "generally solids or thick liquids" in column 3 thereof. Some of the esters disclosed therein are esters of 3,5-dialkyl-4-hydroxyphenylalkanoic acids. One such ester, pentaerythritol tetrakis[3-(3,5-di-t-butyl-4-hydroxyphenyl)propionate], is "a clear amber glass which softens at 50°–60° C." according to Example 6 thereof. In describing an alternative preparation of such compound, that Example refers to a residue which "comprises the product" and states that upon recrystallization "the M.P. is 123°–125° C. A product which is a solid and consists principally of the last-mentioned ester is commercially available from Ciba-Geigy Corporation, Ardsley, N.Y. under the trademark Irganox 1010.

U.S. Pat. No. 3,779,945 (also Dexter, Spivack and Steinberg) discloses physical mixtures of 3-(3,5-dialkyl-4-hydroxyphenyl)propionic acid esters of at least two non-identical alkanediols for stabilization of organic material. In this patent, which issued on a continuation-in-part of Ser. No. 861,475, filed Sept. 26, 1969 (now prior U.S. Pat. No. 3,644,482 supra), the named inventors comment as follows on the esters of 3,5-dialkyl-4-hydroxyphenylalkanoic acids and alkanepolyols described in Ser. No. 861,475: (a) many of the last-mentioned esters are crystalline or vitreous solids; (b) they generally have only limited solubility in solvents employed technically in large amounts, such as aliphatic hydrocarbons; (c) these properties are advantageous in many applications but represent disadvantages in others; and (d) it is extremely difficult to utilize these compounds in technical processes in which the additives are pumped, proportioned and fed in fluid form, for example, in solution polymerization processes.

Dexter et al., U.S. Pat. No. 3,758,549, discloses polyalkanol esters of alkylthioalkanoic acids. The patent discloses that the esters have as their characteristic property the ability to improve the effect of other compounds which are used as stabilizers for organic material normally subject to thermal and oxidative deterioration. Pentaerythritol tetrakis[3-(3,5-di-t-butyl-4-hydroxyphenyl)propionate] (hereinafter sometimes referred to as "pentaerythritol tetrakis-ten" is among the phenolic antioxidants whose stabilizing properties are allegedly improved by the addition of the alkylthioesters. In Example 5 of such patent 0.3% pentaerythritol tetrakis-(3n-dodecylthiopropionate) and 0.1% pentaerythritol tetrakis-ten were blended with polypropylene. According to that example, samples of a sheet prepared from these blended materials exhibited 3170 hours to failure when tested for resistance to accelerated aging in a forced draft oven at 150° C. Apparently by way of comparison, the results tabulated in that example include an entry of 1170 (under the heading "Hours to Failure") opposite an entry of only 0.3% pentaerythritol tetrakis-ten (under the heading "Additive(s)"). Example 9 of such patent discloses a composition comprising linear polyethylene and 0.05 percent by weight of pentaerythritol tetrakis-ten and 0.01 percent by weight of pentaerythritol terakis[3-n-dodecylthiopropionate]. According to the example, bars molded from this composition retained tensile strength for a substantially longer period in a circulating air oven at 120° C., relative to unstabilized linear polyethylene.

A product data bulletin for Seenox TM 412S antioxidant, which is further entitled "pentaerythritol tetrakis(β-laurylthiopropionate)", specifically recommends the product for polypropylene, polyethylene and thermoplastic elastomers. The bulletin states that the product is a crystalline powder which exhibits excellent properties when used in conjunction with a hindered phenolic antioxidant. Heat aging performance is set forth for an extruded and pelletized blend of polypropylene, 0.1% Irganox 1010 and 0.2% Seenox 412S. ("Argus product data" bulletin, Argus Chemical Division, Witco Chemical Corporation, dated 7/80, 3 pages.)

However, heretofore known compounds and mixtures, such as the compounds and mixtures set forth above, have not been entirely satisfactory from such standpoints as ease of handling and efficacy for stabilizing organic material, including polyolefins (e.g., polyethylene and polypropylene) and thermoplastic elastomers, against oxidative and thermal deterioration. Accordingly, there is a substantial need in the art for new compounds having the capability of being easily handled and the capability of stabilizing organic material, including polyolefins and thermoplastic elastomers, against such deterioration or degradation.

It has now been found that the hereinafter described new and improved compounds and mixtures of this invention have such capabilities. When used herein in connection with this invention, the term "oxidative and/or thermal deterioration" and terms of like import include thermo-mechanical deterioration and thermo-oxidative deterioration.

DESCRIPTION OF THE INVENTION

Generally stated, the present invention provides pentaerythritol co-ester compounds having the formula (hereinafter referred to as "Formula A"):

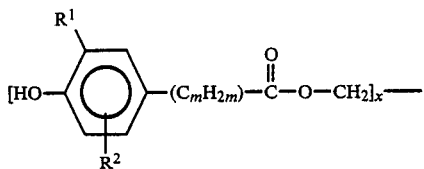

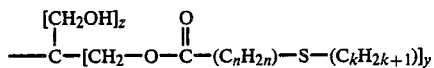

wherein
$R^1$ is methyl, ethyl, an alpha-branched acyclic alkyl group having from 3 to 10 carbon atoms, or a cycloalkyl group having from 5 to 12 carbon atoms;
$R^2$ is hydrogen, methyl, ethyl, an alpha-branched acyclic alkyl group having from 3 to 10 carbon atoms, or a cycloalkyl group having from 5 to 12 carbon atoms and $R^2$ is meta or para to $R^1$;
m is an integer from 1 to about 6;
n is an integer from 1 to about 10;
k is an integer from 1 to about 30;
x is 1, 2 or 3;
y is zero, 1, 2 or 3; and
z is zero, 1 or 2;
subject to the provisos that
 (a) the sum of x, y and z is 4;
 (b) when z is zero, y is 1, 2 or 3 and x is 4—y;
 (c) when z is 2, each of x and y is 1;
 (d) when x is 2 or 3, each $R^1$ is selected independently of each other $R^1$, each $R^2$ is selected independently of each other $R^2$ and each m is selected independently of each other m; and
 (e) when y is 2 or 3, each n is selected independently of each other n and each k is selected independently of each other k.

In another aspect, this invention provides a mixture of at least two non-identical pentaerythritol co-ester compounds. The mixture comprises
(A) a first compound represented by the general Formula A above and
(B) a second compound represented by such general formula provided that the first compound and the second compound are not identical.
Each of x, y, z, each m, each n, each k, each $R^1$ and each $R^2$ in the formula for the first compound is selected independently of x, y, z, each m, each n, each k, each $R^1$ and each $R^2$, respectively, in the formula for the second compound. Each of the first and second compounds can be present in any amount provided that the mixture is effective for stabilizing organic material which is normally susceptible to oxidative and/or thermal deterioration. Each of the compounds may be present in an amount from about 1 or less to about 99 or more percent by weight based on the total weight of the compounds.

In still another aspect of this invention, there are provided organic compositions of matter stabilized against oxidative and/or thermal deterioration, which comprise organic material normally subject to oxidative and/or thermal deterioration and a stabilizing amount of either (i) the compound of Formula A or (ii) the mixture of this invention.

DETAILED DESCRIPTION OF THE INVENTION AND OF THE MANNER AND PROCESS OF MAKING AND USING IT

In the alkylthioalkanoyl moieties, the alkyl groups represented by the formula

in Formula A contain from 1 to about 30 carbon atoms and preferably from about 12 to about 18 carbon atoms, i.e., k is an integer from 1 to about 30 and preferably from about 12 to about 18. Where k is from 3 to about 30, straight and branched chain alkyl groups are included. Illustrative examples of the alkyl groups represented by $C_kH_{2k+1}$ are methyl, ethyl, propyl, pentyl, heptyl, octyl, decyl, dodecyl, tridecyl, tetradecyl, hexadecyl, octadecyl, eicosyl, triacontyl, and the like. The n-dodecyl group is preferred.

The alkylene groups represented by —$(C_nH_{2n})$— in the alkylthioalkanoyl moieties contain from 1 to about 10 carbon atoms, preferably from 2 to 3 carbon atoms and more preferably 2 carbon atoms, i.e., n is an integer from 1 to about 10, preferably from 2 to 3, and more preferably n is 2. Where n is from 3 to about 10, straight and branched chain alkylene groups are included.

Illustrative examples of the alkylthioalkanoyl moieties include:
3-octylthiopropionoyl
3-dodecylthiopropionoyl
3-tridecylthiopropionoyl
3-tetradecylthiopropionoyl
3-hexadecylthiopropionoyl
3-octadecylthiopropionoyl
3-octylthiobutyroyl
3-dodecylthiobutyroyl
3-tridecylthiobutyroyl
3-tetradecylthiobutyroyl
3-octadecylthiobutyroyl
3-octylthioisobutyroyl
3-dodecylthioisobutyroyl
3-octadecylthioisobutyroyl
4-octylthiobutyroyl
4-tridecylthiobutyroyl
4-hexadecylthiobutyroyl
4-octadecylthiobutyroyl
and the like.

Additional illustrative examples of the alkylthioalkanoyl moieties are:
3-methylthiopropionoyl
3-ethylthiopropionoyl
3-propylthiopropionoyl
3-pentylthiopropionoyl
3-heptylthiopropionoyl
3-methylthiobutyroyl
3-ethylthiobutyroyl
3-propylthiobutyroyl
3-pentylthiobutyroyl
3-heptylthiobutyroyl
3-methylthioisobutyroyl
3-ethylthioisobutyroyl
3-propylthioisobutyroyl
3-pentylthioisobutyroyl
3-heptylthioisobutyroyl
4-methylthiobutyroyl
4-ethylthiobutyroyl
4-propylthiobutyroyl
4-pentylthiobutyroyl 4-heptylthiobutyroyl
2-methylthioacetoyl
2-ethylthioacetoyl
2-propylthioacetoyl
2-pentylthioacetoyl
2-heptylthioacetoyl
2-octylthioacetoyl
2-decylthioacetoyl
2-dodecylthioacetoyl
2-tetradecylthioacetoyl
2-hexadecylthioacetoyl
2-octadecylthioacetoyl
5-methylthiovaleroyl
5-octylthiovaleroyl
5-dodecylthiovaleroyl
5-tetradecylthiovaleroyl
5-hexadecylthiovaleroyl
5-octadecylthiovaleroyl
6-methylthiohexanoyl
6-octylthiohexanoyl
6-dodecylthiohexanoyl
6-tetradecylthiohexanoyl
6-hexadecylthiohexanoyl
6-octadecylthiodexanoyl
8-methylthiocapryloyl
8-octylthiocapryloyl
8-dodecylthiocapryloyl
8-tetradecylthiocapryloyl
8-hexadecylthiocapryloyl
8-octadecylthiocapryloyl
10-methylthiodecanoyl
10-octylthiodecanoyl
10-dodecylthiodecanoyl
10-tetradecylthiodecanoyl
10-hexadecylthiodecanoyl
10-octadecylthiodecanoyl and the like. A preferred alkylthioalkanoyl group is the 3-n-dodecylthiopropionoyl group. The alkylthioalkanoyl groups in a single compound represented by Formula A can be the same or different. Thus, where y is 2, the two alkylthioalkanoyl moieties represented by the formula

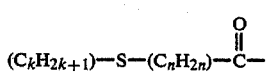

may be, for example, 3-n-dodecylthiopropionoyl and 3-n-octadecylthiopropionoyl groups; and, where y is 3, the three alkylthioalkanoyl moieties may be, for example, 3-n-dodecylthiopropionoyl, 3-n-tetradecylthiopropionoyl and 3-n-octadecylthiobutyroyl groups. Where y is 2 or 3, each alkylthioalkanoyl moiety is preferably the 3-n-dodecylthiopropionyl group.

In regard to $R^1$ and $R^2$ in the mono- or dialkyl-4-hydroxyphenyl alkanoyl moiety represented by the formula portion

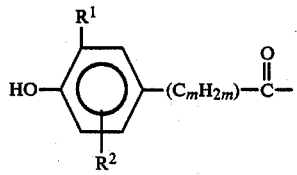

in Formula A, the term "alpha-branched acyclic alkyl group" means an acyclic alkyl group wherein the carbon atom bound to the phenyl group is also bound to at least two other carbon atoms of the acyclic alkyl group. Alpha-branched acyclic alkyl groups from which $R^1$ and $R^2$ may be independently selected include, for example, isopropyl, t-butyl, t-pentyl, t-hexyl and the like. Each of $R^1$ and $R^2$ is preferably t-butyl. As shown by Formula A, $R^1$ is in a position ortho to the hydroxy group. Where $R^2$ is other than hydrogen, $R^2$ is present in the position which is meta to the hydroxy group and para to the $R^1$ group on the same ring or, preferably, in the other position ortho to the hydroxy group. Cycloalkyl groups having from 5 to 12 carbon atoms from which $R^1$ and $R^2$ may be selected include, for example, cyclopentyl, cyclohexyl, cyclooctyl, cyclododecyl and the like.

The mono- or dialkyl-4-hydroxyphenyl group, i.e., the phenolic group, includes, for example:
(a) 3,5-di-t-butyl-4-hydroxyphenyl,
(b) 3,5-di-methyl-4-hydroxyphenyl,
(c) 3,5-di-isopropyl-4-hydroxyphenyl,
(d) 2,5-dimethyl-4-hydroxyphenyl,
(e) 3,5-diethyl-4-hydroxyphenyl,
(f) 3-isopropyl-4-hydroxyphenyl,
(g) 3-t-butyl-4-hydroxyphenyl,
(h) 2-methyl-4-hydroxy-5-t-butylphenyl,
(i) 2-methyl-4-hydroxy-5-isopropylphenyl,
(j) 3-methyl-4-hydroxy-5-t-butylphenyl,
(k) 3-t-phenyl-4-hydroxyphenyl,
(l) 3-t-hexyl-4-hydroxyphenyl,
(m) 3-methyl-4-hydroxyphenyl,
(n) 3-ethyl-4-hydroxyphenyl and the like.

Preferred phenolic groups have at least one alpha-branched alkyl group such as isopropyl, t-butyl or the like in a position ortho to the hydroxy group.

The mono- or dialkyl-4-hydroxyphenyl group is bound to an alkanoyl unit having from 1 to about 7 carbon atoms. The hydrocarbon portion of the alkanoyl unit is represented by $-(C_mH_{2m})-$ and may be a straight chain alkylene group or, when m is from 3 to about 6, a branched chain alkylene unit. Preferably, m is 2 and the alkanoyl group is 3-propionoyl.

A preferred mono- or dialkyl-4-hydroxyphenylalkanoyl group is 3-(3,5-di-t-butyl-4-hydroxyphenyl)propionoyl.

Each of the one, two or three (as determined by the integer x) mono- or dialkylhydroxyphenylalkanoyl groups is bound through an oxygen atom to a carbon atom of pentaerythritol.

The mono- or dialkyl-4-hydroxyphenylalkanoyl groups in any single compound represented by Formula A can be the same or different, i.e., when x is 2 or 3, each $R^1$ is selected independently of each other $R^1$, each $R^2$ is selected independently of each other $R^2$ and each m is selected independently of each other m. Thus, where x is 2, the two mono- or dialkyl-4-hydroxyphenylalkanoyloxy groups represented by the formula

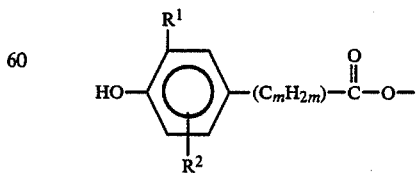

may be, for example, 3-(3,5-di-t-butyl-4-hydroxyphenyl)propionoyloxy and 4-(3-isopropyl-4-hydroxyphenyl)butyroyloxy groups; and where x is 3, the three mono- or dialkyl-4-hydroxyphenylalkanoyloxy groups may be, for example, the two last-mentioned groups and a 3-(3-t-butyl-4-hydroxyphenyl)propionoyloxy group. Where x is 2 or 3, each mono- or dialkyl-4-hydroxyphenylalkanoyloxy group is preferably 3-(3,5-di-t-butyl-4-hydroxyphenyl)propionoyloxy.

Compounds included within Formula A include, for example:

(I) pentaerythritol tris[3-(3,5-di-tert-butyl-4-hydroxyphenyl)propionate]-mono[3-n-dodecylthiopropionate], (II) pentaerythritol bis[3-(3,5-di-tert-butyl-4-hydroxyphenyl)propionate]-bis[3-n-dodecylthiopropionate], (III) pentaerythritol mono[3-(3,5-di-tert-butyl-4-hydroxyphenyl)propionate]-tris[3-n-dodecylthiopropionate], (IV) pentaerythritol tris[3-(3,5-di-tert-butyl-4-hydroxyphenyl)propionate], (V) pentaerythritol bis[3-(3,5-di-tert-butyl-4-hydroxyphenyl)propionate]-mono[3-n-dodecylthiopropionate], (VI) pentaerythritol mono[3-(3,5-di-tert-butyl-4-hydroxyphenyl)propionate]-bis[3-n-dodecylthiopropionate], (VII) pentaerythritol mono[3-(3,5-di-tert-butyl-4-hydroxyphenyl)propionate]-mono-[3-n-dodecylthiopropionate], and the like. These compounds are hereinafter referred to as Compound I, Compound II, Compound III, Compound IV, Compound V, Compound VI and Compound VII, respectively.

Still other compounds included by Formula A above include, for example:

(a) pentaerythritol tris[3-(3,5-dimethyl-4-hydroxyphenyl)propionate]-mono[3-n-dodecylthiopropionate], (b) pentaerythritol tris[3-(3,5-di-isopropyl-4-hydroxyphenyl)propionate]-mono[3-n-dodecylthiopropionate], (c) pentaerythritol tris[3-(2,5-dimethyl-4-hydroxyphenyl)propionate]-mono[3-n-dodecylthiopropionate], (d) pentaerythritol tris[3-(3,5-diethyl-4-hydroxyphenyl)propionate]-mono[3-n-dodecylthiopropionate], (e) pentaerythritol tris[3-(3,5-isopropyl-4-hydroxyphenyl)propionate]-mono[3-n-dodecylthiopropionate], (f) pentaerythritol tris[3-(3-t-butyl-4-hydroxyphenyl)propionate]-mono[3-n-dodecylthiopropionate], (g) pentaerythritol tris[3-(2-methyl-4-hydroxy-5-t-butylphenyl)propionate]-mono[3-n-dodecylthiopropionate], (h) pentaerythritol tris[3-(2-methyl-4-hydroxy-5-isopropylphenyl)propionate]-mono[3-n-dodecylthiopropionate], (i) pentaerythritol tris[3-(3-methyl-4-hydroxy-5-t-butylphenyl)propionate]-mono[3-n-dodecylthiopropionate], (j) pentaerythritol tris[3-(3-cyclopentyl-4-hydroxy-5-t-butylphenyl)propionate]-mono[3-n-dodecylthiopropionate], (k) pentaerythritol tris[3-(3,5-di-cyclododecyl-4-hydroxyphenyl)propionate]-mono[3-n-dodecylthiopropionate], and (l) the analogs of each of the compounds (a) to (k) inclusive wherein each of the 3-(mono- or dialkyl-4-hydroxyphenyl)alkanate groups in those compounds, e.g., the 3-(3,5-dimethyl-4-hydroxyphenyl)propionate group in compound (a), is replaced separately by its corresponding 2-(mono- or dialkyl-4-hydroxyphenyl)acetate,
3-(mono- or dialkyl-4-hydroxyphenyl)butyrate,
3-(mono- or dialkyl-4-hydroxyphenyl)isobutyrate,
4-(mono- or dialkyl-4-hydroxyphenyl)butyrate,
5-(mono- or dialkyl-4-hydroxyphenyl)valerate, and
6-(mono- or dialkyl-4-hydroxyphenyl)hexanate groups.

These analogs include, for example, the 2-(3,5-dimethyl-4-hydroxyphenyl)acetate and 3-(3,5-dimethyl-4-hydroxyphenyl)butyrate analogs of compound (a), i.e., pentaerythritol tris[2-(3,5-dimethyl-4-hydroxyphenyl)acetate]-mono[3-n-dodecylthiopropionate] and pentaerythritol tris[3-(3,5-dimethyl-4-hydroxyphenyl)butyrate]-mono[3-n-dodecylthiopropionate], respectively.

Other illustrative compounds included by Formula A are, for example:

(m) pentaerythritol tris[2-(3,5-di-t-butyl-4-hydroxyphenyl)acetate-mono[3-n-dodecylthiopropionate], (n) pentaerythritol tris[3-(3,5-di-t-butyl-4-hydroxyphenyl)butyrate-mono[3-n-dodecylthiopropionate], (o) pentaerythritol tris[3-(3,5-di-t-butyl-4-hydroxyphenyl)isobutyrate-mono[3-n-dodecylthiopropionate], (p) pentaerythritol tris[4-(3,5-di-t-butyl-4-hydroxyphenyl)butyrate-mono[3-n-dodecylthiopropionate], (q) pentaerythritol tris[5-(3,5-di-t-butyl-4-hydroxyphenyl)valerate-mono[3-n-dodecylthiopropionate], (r) pentaerythritol tris[6-(3,5-di-t-butyl-4-hydroxyphenyl)hexanate-mono[3-n-dodecylthiopropionate], and the like.

It will be apparent to those skilled in the art that each of illustrative compounds (a) to (r) inclusive differs from Compound I solely in the particular mono- or dialkylhydroxyphenylalkanate groups which are present. Similarly, other illustrative compounds are analogs of each of Compounds II to VII inclusive wherein any of the mono- or dialkylphenolic groups in compounds (a) to (r) are present in lieu of any or all of the one, two or three 3,5-di-t-butyl-4-hydroxyphenyl groups which are present in each of Compounds II to VII. Such analogs include, for example, (i) pentaerythritol bis[3-(3,5-dimethyl-4-hydroxyphenyl)propionate]-bis[3-n-dodecylthiopropionate] and (ii) pentaerythritol mono[3-(3,5-di-t-butyl-4-hydroxyphenyl)propionate]-mono[3-(3,5-di-isopropyl-4-hydroxyphenyl)propionate]-bis(3-n-dodecylthiopropionate], which are analogs of Compound II.

Still other illustrative compounds included by Formula A are, for example:

(s) pentaerythritol tris[3-(3,5-di-t-butyl-4-hydroxyphenyl)propionate]-mono[3-methylthiopropionate], (t) pentaerythritol tris[3-(3,5-di-t-butyl-4-hydroxyphenyl)propionate]-mono[3-ethylthiopropionate], (u) pentaerythritol tris[3-(3,5-di-t-butyl-4-hydroxyphenyl)propionate]-mono[3-propylthiopropionate], (v) pentaerythritol tris[3-(3,5-di-t-butyl-4-hydroxyphenyl)propionate]-mono[3-butylthiopropionate], (w) pentaerythritol tris[3-(3,5-di-t-butyl-4-hydroxyphenyl)propionate]-mono[3-pentylthiopropionate], (x) pentaerythritol tris[3-(3,5-di-t-butyl-4-hydroxyphenyl)propionate]-mono[3-hexylthiopropionate], (y) pentaerythritol tris[3-(3,5-di-t-butyl-4-hydroxyphenyl)propionate]-mono[3-heptylthiopropionate], (z) pentaerythritol tris[3-(3,5-di-t-butyl-4-hydroxyphenyl)propionate]-mono[3-octylthiopropionate], (aa) pentaerythritol tris[3-(3,5-di-t-butyl-4-hydroxyphenyl)propionate]-mono[3-decylthiopropionate], (bb) pentaerythritol tris[3-(3,5-di-t-butyl-4-hydroxyphenyl)propionate]-mono[3-tridecylthiopropionate], (cc) pentaerythritol tris[3-(3,5-di-t-butyl-4-hydroxyphenyl)propionate]-mono[3-tetradecylthiopropionate], (dd) pentaerythritol tris[3-(3,5-di-t-butyl-4-hydroxyphenyl)propionate]-mono[3-hexadecylthiopropionate], (ee) pentaerythritol tris[3-(3,5-di-t-butyl-4-hydroxyphenyl)propionate]-mono[3-octadecylthiopropionate], (ff) pentaerythritol tris[3-(3,5-di-t-butyl-4-hydroxyphenyl)propionate]-mono[3-eicosylthiopropionate], (gg) pentaerythritol tris[3-(3,5-di-t-butyl-4-hydroxyphenyl)propionate]-mono[3-docosylthiopropionate], (hh) pentaerythritol tris[3-(3,5-di-t-butyl-4-hydroxyphenyl)propionate]-mono[3-triacontylthiopropionate], (ii) the analogs of each of the compounds (s) to (z) and (aa) to (hh) inclusive wherein each of the 3-alkylthioalkanate groups in those compounds, e.g., the 3-methylthiopropionate group in compound (s), is replaced separately by its corresponding 2-alkylthioacetate, 3-alkylthiobutyrate, 3-alkylthioisobutyrate, 4-alkylthiobutyrate, 5-alkylthiovalerate, 6-alkylthiohexanate, 8-alkylthiocaprylate and 10-alkylthiodecanate groups. These analogs include, for example, the 2-methylthioacetate and 3-methylthiobutyrate analogs of compound (s), i.e., pentaerythritol tris[3-(3,5-di-t-butyl-4-hydroxyphenyl)propionate]-mono[2-methylthioacetate) and pentaerythritol tris[3-(3,5-di-t-butyl-4-hydroxyphenyl)propionate]-mono[3-methylthiobutyrate], respectively.

Other illustrative compounds included by Formula A are, for example:

(jj) pentaerythritol tris[3-(3,5-di-t-butyl-4-hydroxyphenyl)propionate]-mono[2-n-dodecylthioacetate]

(kk) pentaerythritol tris[3-(3,5-di-t-butyl-4-hydroxyphenyl)propionate]-mono[3-n-dodecylthiobutyrate]

(ll) pentaerythritol tris[3-(3,5-di-t-butyl-4-hydroxyphenyl)propionate]-mono[3-n-dodecylthioisobutyrate]

(mm) pentaerythritol tris[3-(3,5-di-t-butyl-4-hydroxyphenyl)propionate]-mono[4-n-dodecylthiobutyrate]

(nn) pentaerythritol tris[3-(3,5-di-t-butyl-4-hydroxyphenyl)propionate]-mono[5-n-dodecylthiovalerate]

(oo) pentaerythritol tris[3-(3,5-di-t-butyl-4-hydroxyphenyl)propionate]-mono[6-n-dodecylthiohexanate]

(pp) pentaerythritol tris[3-(3,5-di-t-butyl-4-hydroxyphenyl)propionate]-mono[8-n-dodecylthiocaprylate] and (qq) pentaerythritol tris[3-(3,5-di-t-butyl-4-hydroxyphenyl)propionate]-mono[10-n-dodecylthiodecanate]

It will be apparent to those skilled in the art that each of illustrative compounds (s) to (z) and (aa) to (qq) inclusive differs from Compound I solely in the particular alkylthioalkanate group which is present. Similarly, other illustrative compounds are analogs of Compounds II, III and V to VII inclusive wherein any of the alkylthioalkanate groups in compounds (s) to (z) and (aa) to (qq) inclusive are present in lieu of any or all of the one, two or three 3-n-dodecylthiopropionate groups which are present in each of Compounds II, III and V to VII inclusive. Such analogs include, for example, (i) pentaerythritol bis[3-(3,5-di-t-butyl-4-hydroxyphenyl)propionate]-bis[3-octadecylthiopropionate], (ii) pentaerythritol bis[3-(3,5-di-t-butyl-4-hydroxyphenyl)propionate]-mono[3-n-dodecylthiopropionate]-mono[3-octylthiopropionate], (iii) pentaerythritol bis[3-(3,5-di-t-butyl-4-hydroxyphenyl)propionate]-bis[2-n-dodecylthioacetate], and (iv) pentaerythritol bis[3-(3,5-di-t-butyl-4-hydroxyphenyl)propionate]-bis[3-n-dodecylthiobutyrate], which are analogs of Compound II.

Still other illustrative compounds included by Formula A are:

(I-a) pentaerythritol tris[2-(3,5-di-t-butyl-4-hydroxyphenyl)acetate]-mono[2-n-dodecylthioacetate], (I-b) pentaerythritol tris[3-(3,5-di-t-butyl-4-hydroxyphenyl)butyrate]-mono[3-n-dodecylthiobutyrate], (I-c) pentaerythritol tris[3-(3,5-di-t-butyl-4-hydroxyphenyl)propionate]-mono[4-n-dodecylthiobutyrate], (I-d) pentaerythritol tris[2-(3,5-di-t-butyl-4-hydroxyphenyl)acetate]-mono[4-n-dodecylthiobutyrate], and (I-e) pentaerythritol tris[2-(3,5-di-t-butyl-4-hydroxyphenyl)acetate]-mono[3-n-dodecylthiopropionate], which are analogs of Compound I, and the corresponding analogs of Compounds II, III and V to VII inclusive.

Each of Compounds I to VII inclusive is the preferred species of its respective subclass of compounds defined by the class of compounds included within Formula A and the particular combination of the values of x, y and z for the respective subclass. The combinations of the values of x, y and z for each of Compounds I to VII inclusive and its corresponding subclass (hereinafter referred to as Subclass I, Subclass II, etc.) are set forth in the following table:

| Subclass | Preferred Compound | x | y | z |
|---|---|---|---|---|
| Subclass I | Compound I | 3 | 1 | 0 |
| Subclass II | Compound II | 2 | 2 | 0 |
| Subclass III | Compound III | 1 | 3 | 0 |
| Subclass IV | Compound IV | 3 | 0 | 1 |
| Subclass V | Compound V | 2 | 1 | 1 |
| Subclass VI | Compound VI | 1 | 2 | 1 |
| Subclass VII | Compound VII | 1 | 1 | 2 |

The compounds in these subclasses are represented by the following formulas:

(Subclass I)

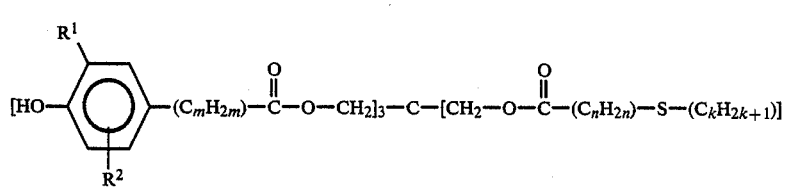

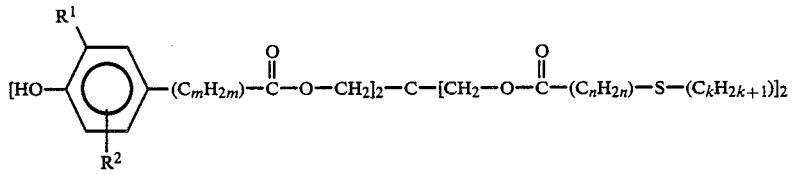
(Subclass II)

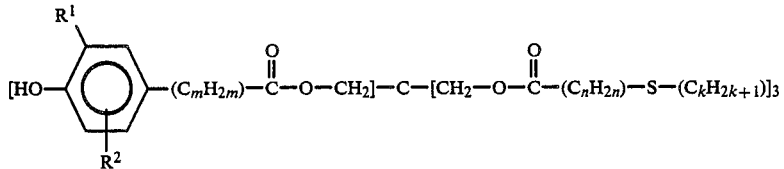
(Subclass III)

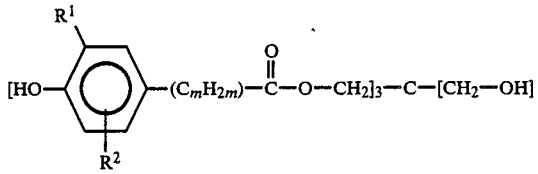
(Subclass IV)

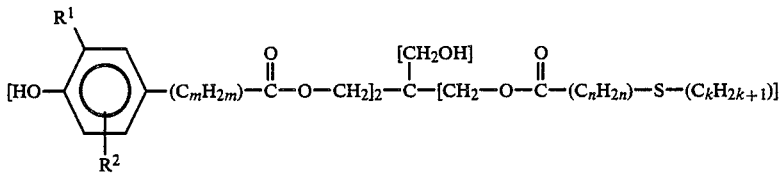
(Subclass V)

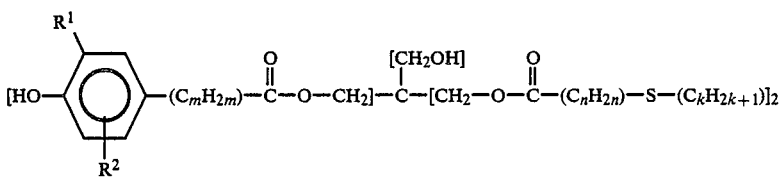
(Subclass VI)

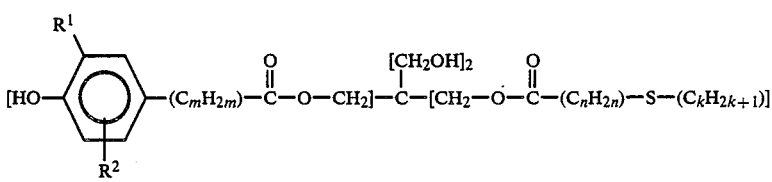
(Subclass VII)

In the compounds included in each such subclass, it is preferred that each $R^1$ is tertiary butyl, each $R^2$ is tertiary butyl and each $R^2$ is meta to the $R^1$ on the same benzene ring. It is also preferred that each m is 2, each n is 2 and each k is 12 in the compounds of each subclass.

Of Compounds I to VII, Compounds I, II and III are preferred. Compounds I and II are more preferred, while Compound II is most preferred for greater versatility.

The compounds of the present invention are useful as stabilizers of organic material normally subject to oxidative and/or thermal deterioration. Such organic material includes, for example, synthetic organic polymeric substances such as vinyl resins formed from the polymerization of vinyl halides or from the copolymerization of vinyl halides with unsaturated polymerizable compounds, e.g., vinyl esters, alpha,beta-unsaturated esters, alpha,beta-unsaturated acids, alpha,beta-unsaturated ketones or aldehydes and unsaturated hydrocarbons such as butadiene and styrene; poly-alpha-olefins such as polyethylene, polypropylene, polybutylene (e.g., polybutene-1), polyisoprene, and the like, including copolymers of alpha-olefins (e.g., linear low density polyethylene); polyurethanes such as those prepared from polyols and organic polyisocyanates; polyamides such as poly(hexamethylene adipamide) and polycaprolactam; polyesters such as poly(methylene terephthalates); polycarbonates; polyacetals; polystyrene; poly(ethylene oxide); and copolymers such as those formed by the copolymerization of acrylonitrile, butadiene and/or styrene; as well as physical mixtures of the foregoing substances such as high impact polystyrene containing copolymers of butadiene and styrene. Other organic materials which can be stabilized by the compounds of the present invention include lubricating oils such as those of the aliphatic ester type, e.g., dihexyl azelate, di-(2-ethylhexyl)azelate, di-(3,5,5,-trimethyl-hexyl)glutarate, di(3,5,5-trimethylpentyl)glutarate, di-(2-ethylhexyl)pimelate, di-(2-ethylhexyl)-adipate, diisoamyl adipate, triamyl tricarballate, pentaerythritol tetracaproate, dipropylene glycol dipelargonate, 1,5-pentanediol di-(2-ethylhexanoate), and the like; fats and oils of animal and vegetable origin, e.g., linseed oil, menhaden oil, cod liver oil, castor oil, olive oil, rapeseed oil, coconut oil, palm oil, corn oil, sesame oil, peanut oil, cotton seed oil, butter, fat, lard, beef tallow and the like; saturated and unsaturated hydrocarbons such as for example, both natural and synthetic gasolines, jet fuels, diesel oils, mineral oils, fuel oils, drying oils, waxes and resins.

The stabilizers of this invention (including the compounds represented by Formula A above and mixtures thereof) may be employed in any stabilizing amount as stabilizers for organic materials normally susceptible to oxidative and/or thermal deterioration. Such amount may be for example, from about 0.005% to about 10% by weight of the stabilized composition. For polyolefins, e.g., linear low density polyethylene, polypropylene and poly(butene-1), such amount is preferably from about 0.01% to about 5% and more preferably from about 0.05% to about 1%. For styrene-diene-styrene block copolymers, e.g., such copolymers containing one or more blocks of polybutadiene or polyisoprene, such amount is preferably from about 0.005% to about 10% and more preferably from about 0.1% to about 1%.

The stabilizers of this invention may be used alone or in combination with other stabilizers or additive materials, such as dilauryl-beta-thiodipropionate, distearyl-beta-thiodipropionate, pentaerythritol tetrakis-ten, pentaerythritol tetrakis(beta-laurylthiopropionate), mixtures thereof and the like.

Other antioxidants, antiozonants, thermal stabilizers, ultraviolet light absorbers, coloring materials, dyes, pigments, metal chelating agents, etc. may also be used in the compositions of the invention.

Phosphite esters may also be used in stabilized compositions containing the novel stabilizer compounds of the present invention. Such phosphite esters include dialkyl phosphites (for example, distearyl phosphite, dilauryl phosphite, and the like); trialkyl phosphites (for example, trilauryl phosphite, tris(ethylhexyl)phosphite, and the like); and tris(alkaryl)phosphites (for example tris(nonylphenyl)phosphites, and the like).

The stabilizers of this invention are especially useful for stabilizing polymeric materials such as polyolefins, e.g., polyethylene (especially linear low density polyethylene, i.e., LLDPE), polypropylene, poly(butene-1), and the like; and styrene-diene block copolymers, e.g., styrene-butadiene-styrene and styrene-isoprene-styrene block copolymers (especially such block copolymers which are thermoplastic elastomers).

Stabilized compositions of matter of this invention may be prepared by incorporating the stabilizer into the organic material to be stabilized using well known methods for incorporating stabilizers into such material. In general, the stabilizer may simply be physically admixed with the organic material.

The compounds of this invention can be prepared by esterification of pentaerythritol, C(CH$_2$OH)$_4$, with both (a) at least one mono- or dialkyl-4-hydroxyphenylalkanoic acid of the formula (hereinafter "Formula B"):

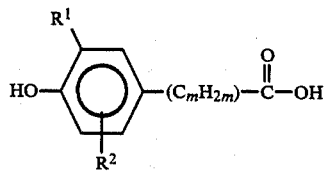

(B)

wherein R$^1$, R$^2$ and m are as defined above and (b) at least one alkylthioalkanoic acid of the formula (hereinafter "Formula C"):

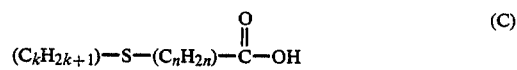

wherein k and n are as defined above or acid chlorides or lower alkyl esters of such acids. Esterification is preferably carried out concurrently with (i) the above acids, (ii) acid chlorides thereof or (iii) lower alkyl esters thereof. Direct esterification with the acids is conducted in the presence of an acidic catalyst such as p-toluenesulfonic acid. Water formed by the reaction is removed, preferably continuously, as by distillation.

When acid chlorides of the above acids are utilized, the reaction is generally conducted in the presence of an acid scavenger such as pyridine, which can serve as the reaction medium. A solvent, such as toluene or chloroform, is additionally and advantageously employed to improve solubility of the reactants in the reaction medium.

When lower alkyl esters of the above acids are used, the reaction is carried out in the presence of a transesterification catalyst such as a hydride or lower alkoxide of an alkali metal, such as lithium hydride, lithium hydroxide, sodium methoxide, potassium-t-butoxide, mixtures thereof and the like. These catalysts are employed in a catalytically effective amount, preferably from about 0.01 to about 0.3 mole equivalent per mole of pentaerythritol. Sodium methoxide is preferred.

Preparation of the compounds of this invention is preferably carried out by transesterification of pentaerythritol with lower alkyl esters of the above acids such as the methyl and ethyl esters thereof. The methyl esters are preferred. The transesterification reaction is carried out under transesterification conditions, including elevated temperature and the presence of a transesterification catalyst in a catalytically effective amount. Preferably, the transesterification reaction is carried out in a solution containing the reactants and at least a solubilizing amount of an inert solvent for at least one, and preferably all, of the reactants and a transesterification catalyst. Dimethyl formamide (DMF) is preferred as the inert solvent. However, an inert solvent is optional.

Many of the mono- or dialkyl-4-hydroxyphenyl alkanoic acids of Formula B and lower alkyl esters thereof, e.g., methyl and ethyl 3-(3,5-di-tert-butyl-4-hydroxyphenyl)propionate, are susceptible to deterioration under the reaction conditions employed in preparing the compounds of Formula A. These acids and lower alkyl esters are advantageously stabilized against such deterioration by adding heretofore known stabilizers, e.g., phenolic stabilizers such as pentaerythritol tetrakis-ten. Such stabilizers may be separately admixed with the acids or lower alkyl esters (or mono- or dialkyl-phenol precursors thereof, e.g., mono- or dialkyl-phenols), added directly to reaction mixtures employed in preparing the compounds of this invention or combinations of these methods may be used. The phenolic stabilizer may be employed in any stabilizing amount, for example from about 0.01 to about 0.1 mole equivalent of the phenolic hydroxyl groups thereof per mole of the acid or lower alkyl ester (or mono- or dialkyl-phenol precursor).

The transesterification reaction may be carried out at any suitable temperature, e.g., from about 80° C. to about 220° C., and any suitable pressure, e.g., from about 0.1 to about 760 mm Hg or more, for any suitable period, e.g., from about 3 hours or less to about 20 hours or more. Although the time required for completion of the reaction is dependent upon the particular reactants and concentrations thereof, catalyst and concentration thereof, solvent, temperature, and pressure employed, the reaction is, in general, substantially complete within about 6 to about 10 hours.

The transesterification reaction is preferably carried out in two phases. In the initial or first phase the reaction is preferably carried out with stirring and (a) under an inert gaseous blanket, i.e., at least substantially inert to the reactants, catalyst, and solvent which are employed and to the products which are formed and (b) at atmospheric pressure (i.e., about 760 mm Hg). Nitrogen is the preferred inert gaseous medium. A flow of nitrogen or other inert gaseous medium is preferably passed through the vapor zone above the liquid reaction mixture, thereby removing the lower alkanol which forms during the transesterification. The first phase of the reaction is concluded upon removal of the lower alkanol in a total mole equivalent amount corresponding to 25 to 50% or more of the lesser of (a) the total mole equivalents of —OH groups in the initially present pentaerythritol and (b) the total mole equivalents of carboxyalkyl groups in the initially present lower alkyl esters. Removal of such amount generally occurs within about 3 to about 5 hours.

Thereafter, in the second phase the reaction is continued, preferably with stirring, under reduced pressure with or without the presence of an inert gaseous blanket. Reduced pressure is employed for the purpose of removing solvent and lower alkanol and increasing the amount of the desired resulting product. A suitable reduced pressure for the second phase is about 50 mm Hg absolute or less, e.g., 20 to about 50 mm Hg absolute. Although pressures below 20 mm Hg absolute are effective, the resulting advantages are generally insufficient to offset the added cost thereof. The second phase of the reaction is, in general, concluded within about 3 to about 8 hours.

The mole ratio of the lower alkyl ester of the mono- or dialkylhydroxyphenylalkanoic acid of Formula B (hereinafter sometimes referred to as the phenolic acid) to the lower alkyl ester of the alkylthioalkanoic acid of Formula C (hereinafter sometimes referred to as the sulfur-containing acid) in the reaction mixture may be from about 0.8:1 to about 1.2:1, preferably 1:1.

The total molar ratio, i.e., the ratio of (a) the total moles of (i) lower alkyl ester of phenolic acid plus (ii) lower alkyl ester of sulfur-containing acid to (b) pentaerythritol may be, for example, from about 4.8:1 or more to about 1.6:1. The total molar ratio is preferably about 4.08:1.

Where the mole ratio of the phenolic acid ester of Formula B to the sulfur-containing acid ester of Formula C is from about 0.8:1 to about 1.2:1, total molar ratios of more than 4:1 and long reaction time (e.g., 5 to 6 hours or more in the first and second phases of the reaction) in general result in increasing the amounts of compounds of Formula A where (a) x is 3 and y is 1, (b) x is 2 and y is 2 and (c) x is 1 and y is 3, e.g., (a) Compound I, (b) Compound II and (c) Compound III, respectively.

In general, increased amounts of compounds of Formula A where x is 2 and y is 2, for example Compound II (most preferred compound of this invention), result from carrying out the transesterification reaction using, in combination, high concentration of lower alkoxide of alkali metal as catalyst (e.g., about 0.2 mole equivalent of sodium methoxide or potassium tert-butoxide per mole of pentaerythritol); long reaction time (e.g., at least a total of 10 hours); high reaction temperature (e.g., at least 135° C.); and very low pressure in the second phase of the reaction (e.g., 5 to 20 mm Hg)—as illustrated in greater detail in Example 1 below.

It is found that mixtures of two or more compounds of Formula A typically result from the transesterification. For many applications the two or more resulting compounds of Formula A need not be separated since the reaction-product mixtures are highly effective stabilizers. In general, other stabilizers which may have been present in the reaction mixture during the transesterification need not be removed from the resulting reaction-product mixture prior to stabilizing organic material with the mixture. If desired, one or more compounds of Formula A may be recovered from such mixtures and used separately as stabilizers. Two or more recovered compounds may be admixed to form effective stabilizer mixtures as desired. Admixing may be effected by adding the desired compounds to a solvent therefor (e.g., hexane, acetone, or toluene) with stirring and removing the solvent from the resulting solution, preferably under reduced pressure. Admixing may also be effected using well-known methods for liquid blending, preferably at a temperature (e.g., 50° to 80° C.) effective for reducing viscosity of the compounds.

In another aspect of this invention, as indicated above there is provided a mixture of at least two non-identical compounds of the invention. The mixture comprises (A) a first compound represented by the general Formula A above and (B) a second compound represented by such general formula provided that the first compound and the second compound are not identical. Each of x, y, z, each m, each n, each k, each $R^1$ and each $R^2$ in the formula for the first compound is selected independently of x, y, z, each m, each n, each k, each $R^1$ and each $R^2$, respectively, in the formula of the second compound. Each of the first and second compounds may be present in an amount, for example, from about 1 or less to about 99 or more percent by weight based on the total weight of the compounds. Each of the first and second compounds can be present in any amount provided that the mixture is effective for stabilizing organic material normally susceptible to oxidative degradation. There are no known numerical limits on the proportions in which the compounds of this invention may effectively be present in the mixture of this invention.

In a preferred mixture of this invention, the first and second compounds are compounds of Subclass I and Subclass II, respectively. This mixture is hereinafter referred to as "Mixture A". In these compounds it is preferred that each $R^1$ is tertiary butyl, each $R^2$ is tertiary butyl and each $R^2$ is meta to the $R^1$ on the same ring. It is also preferred that each m is 2, each n is 2 and each k is 12 in these compounds. Advantageously, the second compound is present in an amount from about 0.2 part to about 3.2 parts by weight per one part by weight of the first compound. The first and second compounds are preferably Compound I and Compound II, respectively.

Mixture A may further include a compound of Subclass III as a third compound. Where the third compound is included, the mixture is hereinafter referred to as "Mixture A-1". Each of $R^1$, and $R^2$, m, each n and each k in the formula for the third compound is selected independently of each other $R^1$, $R^2$, m, n and k in the formulas for the first and second compounds. Each of the first, second and third compounds may be present in an amount, for example, from about 1 or less to about 99 or more percent by weight based on the total weight of these compounds. It is preferred that each $R^1$ is tertiary butyl, each $R^2$ is tertiary butyl and each $R^2$ is meta to the $R^1$ on the same ring in these compounds. It is also preferred that each m is 2, each n is 2 and each k is 12 in these compounds. Advantageously, the second compound is present in an amount from about 0.2 part to about 3.2 parts by weight per one part by weight of the first compound, and the third compound is present in an amount from about 0.05 part to about 2.6 parts by weight per one part by weight of the first compound. The first, second and third compounds are preferably Compound I, Compound II and Compound III, respectively.

Mixture A-1 may further include at least one 2-(tri-substituted)ethanol compound selected from the compounds of Subclass IV, Subclass V and Subclass VI as at least one additional compound. In the formulas for the compounds from which the one or more additional compounds are selected and the formulas for the first, second and third compounds, each $R^1$ is selected independently of each other $R^1$, each $R^2$ is selected independently of each other $R^2$, each m is selected independently of each other m, each n is selected independently of each other n and each k is selected independently of each other k. Each included compound may be present in an amount, for example, from about 1 or less to about 99 or more percent by weight based on the total weight of the included compounds. In an advantageous embodiment, Mixture A-1 further includes at least two such additional compounds, including at least one compound from each of two different subclasses among Subclass IV, Subclass V and Subclass VI. In another advantageous embodiment, Mixture A-1 includes at least three such additional compounds, including at least one compound from each of Subclass IV, Subclass V and Subclass VI. In the last-mentioned embodiment the mixture is hereinafter referred to as "Mixture A-2". In each of these additional-compound mixtures, it is preferred that each $R^1$ is tertiary butyl, each $R^2$ is tertiary butyl and each $R^2$ is meta to the $R^1$ on the same ring in the included compounds. It is also preferred that each m is 2, each n is 2 and each k is 12 in the included compounds. Advantageously, in Mixture A-2, per one part by weight of the first compound, the second compound is present in an amount from about 0.2 part to about 3.2 parts by weight, the third compound is present in an amount from about 0.05 part to about 2.6 parts by weight, the compound of Subclass IV is present in an amount from about 0.01 part to about 4.4 parts by weight, the compound of Subclass V is present in an amount from about 0.05 part to about 5.8 parts by weight and the compound of Subclass VI is present in an amount from about 0.1 part to about 10 parts by weight. Compound IV, Compound V and Compound VI are the preferred compounds of Subclass IV, Subclass V and Subclass VI, respectively, in these additional-compound mixtures.

Mixture A-2 may further include a compound of Subclass VII as a still further included compound. In the formulas for this compound and the other compounds included in this embodiment, each $R^1$ is selected independently of each other $R^1$ and each $R^2$ is selected independently of each other $R^2$. It is preferred that each $R^1$ is tertiary butyl, each $R^2$ is tertiary butyl and each $R^2$ is meta to the $R^1$ on the same ring in the included compounds. It is also preferred that each m is 2, each n is 2 and each k is 12 in these compounds. Advantageously, in this mixture per one part by weight of the first compound, the second compound is present in an amount from about 0.2 part to about 3.2 parts by weight, the third compound is present in an amount from about 0.05 part to about 2.6 parts by weight, the compound of Subclass IV is present in an amount from about 0.01 part to about 4.4 parts by weight, the compound of Subclass V is present in an amount from about 0.05 part to about 5.8 parts by weight, the compound of Subclass VI is present in an amount from about 0.1 part to about 10 parts by weight and the compound of Subclass VII is present in an amount up to about 1.8 parts by weight, e.g., from about 0.01 to about 1.8 parts by weight. In Mixture A-2 the optionally included compound of Subclass VII is preferably Compound VII.

In general, compounds of Subclasses I through VII (e.g., Compounds I through VII) may be present in reaction-product mixtures resulting from transesterification of pentaerythritol with lower alkyl esters of the acids of Formulas B and C in the amounts, per one part of compound(s) of Subclass I, set forth in column (a) of the table below. Preferred amounts and more preferred amounts are set forth in columns (b) and (c), respectively, of the table.

| Subclass | Approximate Parts | | |
| --- | --- | --- | --- |
| | (a) | (b) | (c) |
| I | 1.0 | 1.0 | 1.0 |
| II | 0.2–3.2 | 0.4–2.2 | 0.9–1.8 |
| III | 0.05–2.6 | 0.1–1.3 | 0.5–0.7 |
| IV | 0.01–4.4 | 0.05–1.0 | 0.1–0.3 |
| V | 0.05–5.8 | 0.1–2.0 | 0.2–0.5 |
| VI | 0.1–10.0 | 0.15–2.5 | 0.2–0.8 |
| VII | 0–1.8 | 0–0.9 | 0–0.1 |

General Separation Procedure

One or more compounds of Formula A can be recovered from reaction mixtures containing two or more of such compounds prepared as described above using the following preferred recovery methods.

Compounds I, II and III

Compounds I, II and III (and/or analogs thereof having like combinations of the values of x, y and z) can be recovered as follows. To the top of a vertical column packed with 10 parts by weight of silica gel (230–400 mesh) and filled with methylene chloride is introduced a solution of one part by weight of the reaction mixture being separated in one part by volume of methylene chloride. The introduced solution is thereafter eluted by introducing an eluting volume (e.g., about 50 parts by volume) of methylene chloride effective for preferentially eluting, as a group, Compounds I, II and III (and-/or the above analogs thereof) to the substantial exclusion of alcoholic compounds such as Compounds IV, V, VI and VII (and analogs thereof having like combinations of values of x, y and z). Effective eluting volumes can readily be determined for any given set of conditions from analysis of the eluted material, as by analytical high performance liquid chromatography (HPLC). The resulting eluted solution is collected and methylene chloride is removed therefrom under reduced pressure.

The resulting residue is dissolved in methylene chloride (e.g., about 1.7 parts by volume per one part residue). The resulting solution is injected into a preparative HPLC device equipped with a silica gel column, e.g., a "Waters Prep 500 HPLC" (commercially available from Waters Company, Millford, Mass. and equipped with a "Silica Prep Pak 500" column). Thereafter, the injected solution is eluted with a high-pressure flow of methylene chloride (at a rate of 100 ml per minute for the above Waters Prep 500 HPLC). The course of the elution is monitored by refractive index and the resulting separately eluted fractions of the separate compounds in methylene chloride are separately recovered. Methylene chloride is thereafter removed from the various fractions under reduced pressure to yield the desired separate products, e.g., Compound I, Compound II and Compound III, as separate residues. Product purity can be increased by separately repeating the foregoing preparative HPLC procedure for each separate residue.

Compounds IV, V, VI and VII

Compounds IV, V, VI and VII (and analogs thereof having like combinations of values of x, y and z) can be recovered in a modification of the above separation method as follows. After Compounds I, II and III (and/or analogs thereof) are eluted from the vertical column, the alcoholic Compounds IV, V, VI and VII (and/or the foregoing analogs thereof) are eluted as a group with an eluting volume of ethyl acetate in lieu of the eluting volume of methylene chloride. The resulting eluted solution is introduced into the top of a like column packed with a fresh supply of 10 parts of like silica gel and eluted with an eluting volume (e.g., about 200 parts by volume) of a mixture of 99% methylene chloride and 1% acetonitrile. A first eluted fraction, a solution rich in Compounds IV, V and VI (and/or their foregoing analogs) as determined by analytical HPLC, is collected. If the mixture contains Compound VII (and/or one or more analogs thereof having like combinations of the values of x, x and z), the column is thereafter eluted with an eluting volume (e.g., about 100 parts by volume) of a mixture of 70% methylene chloride and 30% acetonitrile, thereby eluting a second fraction, which is rich in Compound VII (and/or its above one or more analogs). Solvent in the second fraction is removed under reduced pressure to yield a residue rich in Compound VII and/or its above one or more analogs.

The first-fraction solution is effectively concentrated by partial solvent removal, injected into a preparative HPLC device, e.g., a Waters Prep 500 HPLC, and thereafter eluted as above except using a solvent mixture of 98% methylene chloride and 2% acetonitrile in lieu of methylene chloride as the high-pressure flow. The course of the elution is monitored by analytical HPLC and the resulting separately eluted fractions of the separate compounds in the solvent mixture are separately recovered. Removal of solvent mixture from the recovered fractions under reduced pressure yields the desired separate products, e.g., Compound IV, Compound V and Compound VI, as separate residues. Product assay can be increased by separately repeating this preparative HPLC procedure for each separate residue.

The above-described second fraction from the vertical column is similarly subjected to preparative HPLC except using a solvent mixture of 90% methylene chloride and 10% acetonitrile as the high-pressure flow, thereby yielding a product of higher assay in, e.g., Compound VII.

The stabilizers of this invention, i.e., the compounds and mixtures thereof, generally are highly soluble, moderately viscous liquids (at 23° C. and higher temperatures) which, as such, advantageously can be added to organic material with substantially greater ease and control of the addition than solid compounds and solid mixtures thereof such as those which have heretofore been proposed for stabilizing organic polymeric substances and other organic materials. The hereindescribed mixtures comprising Compounds I to VI, including and not including Compound VII, have unexpectedly been found to be highly soluble in aliphatic hydrocarbons (including for example hexane) and other organic solvents employed technically in large smounts (e.g., toluene, acetone, chloroform and methanol). For example, the mixtures set forth in the Examples below have unexpectedly and advantageously been found to be soluble at 23° C. in amounts exceeding 100 grams per 100 grams in hexane, toluene, acetone and chloroform and approximately 30 grams or more in methanol on the same basis, while advantageously being essentially insoluble in water (less than 0.01 gram, same basis). The stabilizers of this invention are highly adapted for use in technical processes which require or prefer pumping, proportioning or feeding additives in fluid form, for example, in solution polymerization processes. Accordingly, this invention overcomes the disadvantages noted above and mentioned by Dexter, Spivack and Steinberg in U.S. Pat. No. 3,779,945 in commenting on the esters described in their U.S. Pat. No. 3,644,482.

The lower alkyl ester of phenolic acid and the lower alkyl ester of sulfur-containing acid employed as reactants in the transesterification may be mixtures of two or more lower alkyl esters of phenolic acid and mixtures of two or mor lower alkyl esters of sulfur-containing acid, respectively. Such mixtures result in compounds of Formula A having two or more different mono- or dialkylhydroxyphenylalkanoyl moieties and two or more different alkylthioalkanoyl moieties.

The acids of Formula B and lower alkyl esters thereof, many of which acids and esters are known, can be readily synthesized from alkylated phenols. Acids of Formula B where m is 1 can be prepared, for example, by chloromethylation of alkylphenols (e.g., the alkylphenols described as starting materials by Filbey in U.S. Pat. No. 2,838,571) followed by reaction of the resulting intermediates with sodium or potassium cyanide and hydrolysis of the resultant alkylhydroxyphenylacetonitriles. Such preparation is illustrated in greater detail in Izv. Akad. Nauk SSSR, Ser. Khim, 1965(2) pages 376–378 (V. V. Ershov and I. S. Belostotskaya) and in "Synthesis of hydroxyphenylacetic acids of the hindered phenol series," Chemical Abstracts, Vol. 62, 1965, 14563h–14564a, which is incorporated herein by reference. The lower alkyl esters of acids of Formula B where m is 2 can be prepared by reaction of carbanions of alkylphenols with lower alkyl esters of acrylic acid in accordance with the method described by Dexter et al., U.S. Pat. No. 3,247,240. The acids of Formula B where m is 3 or more can be readily prepared by Friedel-Crafts alkylation of alkylphenols with lower alkyl esters of chloroformylalkanoic acids, hydrolysis of the resulting esters to the corresponding acids and reduction of the resulting acids as, for example, through a Clemmensen reduction. The lower alkyl esters of the acids of Formula B where m is 3 or more can be prepared by reduction of the esters resulting from the above-described Friedel-Crafts alkylation as, for example through a Clemmensen reduction.

The acid chlorides of the acids of Formula B are obtained from the acids through the use of thionyl chloride while the corresponding lower alkyl esters are obtained as described above or from the acids through well-known esterification methods.

Typical of the various pathways for the preparation of these starting materials are the following procedures:

(A) Methyl 3-(3,5-di-t-butyl-4-hydroxyphenyl)propionate (hereinafter sometimes referred to as "MHCE").

To 500 parts by volume of dry t-butyl alcohol in a flask fitted with mechanical stirrer, inert gas inlet, thermometer, condenser and dropping funnel are added 2.1 parts of potassium metal. After the ensuing reaction is complete, there are added 37.3 parts of 2,6-di-t-butylphenol, followed rapidly by 17.7 parts of methyl acrylate. The stirred reaction mixture is heated to 50° C. for 18 hours and allowed to cool. The solvent is removed under reduced pressure and the residual mass neutralized by addition of dilute hydrochloric acid. This mixture is then extracted with two portions of 200 parts by volume each of ethyl ether. The combined ethereal extracts are washed with two portions of 100 parts by volume each of water and then dried over anhydrous sodium sulfate. The ether layer is removed by filtration and concentrated on a steam bath. The residual oily mass is then vacuum distilled. The fraction collected at 125°–130° C./0.1 mm Hg crystallizes upon standing to yield methyl 3-(3,5-di-t-butyl-4-hydroxyphenyl)propionate, M.P. 63.0°–64.5° C. Recrystallization from hexane yields a white solid, M.P. 66°–66.5° C.

Substitution of 2-methyl-6-t-butylphenol, 2,6-di-isopropylphenol, 2-t-butyl-5-methylphenol, 2-t-butylphenol and 2-cyclohexylphenol for 2,6-di-t-butylphenol in the above procedure yields methyl 3-(3-methyl-4-hydroxy-5-t-butylphenyl)propionate, B.P. 136°–144° C./0.02 mm Hg, methyl 3-(3,5-di-isopropyl-4-hydroxyphenyl)propionate, B.P. 130°–132° C./0.4 mm Hg, methyl 3-(2-methyl-4-hydroxy-5-t-butylphenyl)propionate, M.P. 75.5°–77.5° C., methyl 3-(3-t-butyl-4-hydroxyphenyl)propionate, M.P. 146°–147° C., and methyl 3-(3-cyclohexyl-4-hydroxyphenyl)propionate, respectively. Substitution of ethyl acrylate for methyl acrylate in the above procedure yields the corresponding ethyl esters, e.g., ethyl 3-(3,5-di-t-butyl-4-hydroxyphenyl)propionate (hereinafter sometimes referred to as "EHCE"). An alternative pathway for preparing MHCE is as next described. The above typical pathway or procedure for preparing MHCE is followed except that the amount of t-butyl alcohol is 8.5 parts by weight; potassium tert-butoxide (0.6 part) is added in lieu of the potassium metal, thereby obviating the "ensuing reaction" of the typical procedure; there are added about 0.04 part of hydroquinone concurrently with the 2,6-di-t-butylphenol addition, which is the first step in the alternative pathway; the amount of methyl acrylate added is about 25.5 parts; the stirred reaction mixture is heated to about 87° C. until at least a desired portion (e.g., 90%) of the added 2,6-di-t-butylphenol is converted to MHCE (as determined by high performance liquid chromatographic analysis of the mixture). The MHCE-containing residual mass which results from removing solvent (i.e., t-butyl alcohol) under reduced pressure was used as the source of MHCE for preparing MHCE-derived compounds of Formula A in the Examples set forth below, without using (nor need for) the subsequent steps (neutralization through recrystallization) set forth in the above-described typical procedure. Substitution of an equimolar amount of ethyl acrylate for methyl acrylate in the alternative pathway for preparing MHCE results in an alternative pathway for preparing EHCE. In like manner, the EHCE-containing residual mass resulting from solvent removal was used as the source of EHCE in the Examples below. It is understood that the solvent removal step also results in removing remaining acrylate ester in these alternative pathways.

(B) Ethyl alpha-(3,5-di-t-butyl-4-hydroxyphenyl)isobutyrate.

To 200 parts by volume of dry t-butyl alcohol in a suitable flask fitted with mechanical stirrer, inert gas inlet, thermometer, condenser and dropping funnel is added 22.4 parts of potassium t-butoxide, 41.2 parts of 2,6-di-t-butylphenol and 50 parts by volume of triethylene glycol dimethyl ether. The dark green solution is stirred and a solution of an equimolar portion of ethyl alpha-bromo-alpha-methylpropionate in 50 parts of t-butyl alcohol is added dropwise over 20–60 minutes. After addition is complete, the reaction is refluxed for 1 hour, the solution then being neutral. The reaction mixture is poured into water and extracted with ether. The ethereal solution is washed with water and dried and the ether removed by distillation, the product being isolated by vacuum distillation. The corresponding methyl ester, which is alternatively named as methyl 2-(3,5-di-t-butyl-4-hydroxyphenyl)-2,2-dimethylacetate, is similarly obtained from methyl alpha-bromo-alpha-methylpropionate.

In a similar fashion, utilizing ethyl alpha-bromopropionate, there is obtained ethyl 2-(3,5-di-t-butyl-4-hydroxyphenyl)propionate, M.P. 54°–56° C.

(C) 7-(3-methyl-5-t-butyl-4-hydroxyphenyl)heptanoic acid.

To a cooled (−5° C.) solution of 103 parts of ethyl 6-chloroformyl hexanoate in 100 parts by volume of ethylene chloride is rapidly added with stirring 133 parts of granular anhydrous aluminum chloride. To this mixture is next added a solution of 88 parts of 2-methyl-6-t-butylphenol in 500 parts by volume of ethylene chloride. The reaction mixture is stirred at −5° C. for 5 hours and then allowed to slowly attain room temperature overnight. At the end of this time the material is poured over ice, rendered acidic with 6N hydrochloric acid and extracted with ether. The combined extracts are successively washed with water, dilute aqueous sodium bicarbonate solution and saturated aqueous sodium bicarbonate solution. After drying over sodium sulfate, the solvent is removed under reduced pressure to yield ethyl 6-(3-methyl-5-t-butyl-4-hydroxybenzoyl)-hexanoate, which is saponified with excess potassium hydroxide in methanol. After acidification of the reaction mixture, the solid, comprising 6-(3-methyl-5-t-butyl-4-hydroxybenzoyl)hexanoic acid, is subjected to a Clemmenson reduction as modified by Martin [J.A.C.S. 58, 1438 (1936)] to yield 7-(3-methyl-5-t-butyl-4-hydroxyphenyl)heptanoic acid which is esterified with ethanol and p-toluenesulfonic acid to yield the corresponding ethyl ester.

In a modification of this Friedel-Crafts reaction, 2,6-di-methylphenol is treated with acrylonitrile in the presence of aluminum chloride to yield 3-(3,5-dimethyl-4-hydroxyphenyl)propionitrile. Upon hydrolysis of this and esterification of the resulting free acid with methanol and p-toluenesulfonic acid, there is obtained methyl 3-(3,5-di-methyl-4-hydroxyphenyl)propionate, M.P. 70°–83° C.

The lower alkyl esters of the acids of Formula C, e.g., methyl 3-n-dodecylthiopropionate, can be prepared for all combinations of the values of n and k where n is from 2 to about 10 by reacting an alkyl mercaptan of the formula $$(C_kH_{2k+1})-SH$$

wherein k is as defined above, with a lower alkyl ester of an alpha-alkenoic acid (i.e., a lower alkyl alkenate) of the formula $$CH_2=CH-(CH_2)_r-\overset{O}{\underset{\|}{C}}-O-R^3$$

wherein r is an integer equal to n<2, n is as defined above and $R^3$ is a lower alkyl group such as methyl or ethyl. Where n is 2, r is zero and the $CH_2=CH-$ group is attached directly to the carbonyl carbon atom. The reaction, which is exothermic, is carried out by slowly adding a stoichiometric excess of the lower alkyl alkenate to the alkyl mercaptan in the presence of a catalyst effective for promoting the following overall thiol-alkene reaction:

$$-SH+CH_2=CH-\longrightarrow -S-CH_2-CH_2-$$

When n in Formula C is 2, the catalyst is an alkali metal alkoxide, preferably sodium methoxide. When n is 3 or more, a free radical generator such as a peroxide or an azonitrile (preferably 2,2'-azo-bis-isobutyronitrile) is the catalyst. The reaction is carried out with stirring at any suitable temperature, e.g., about 20°–30° C., and any suitable pressure, e.g., 760 mm Hg, for a sufficient period, e.g., up to about 20 hours or more, to effect the desired extent of reaction. The heat of reaction is removed using well known procedures for controlling the temperature of exothermic reactions. Where the alkyl mercaptan cannot be readily stirred at the reaction temperature employed, the reaction can be carried out in the presence of a solubilizing liquid medium which is inert to the reactants, e.g., chloroform. The catalyst is preferably employed in an amount of about 0.05 mole per mole of the alkyl mercaptan.

By way of illustration, methyl 3-n-dodecylthiopropionate can be prepared substantially in accordance with the method set forth by Stephens et al., J. Am. Chem. Soc., Vol. 73 (1951) at page 4050, as next described. Methyl acrylate (86.1 grams, 1.0 mole) is slowly added dropwise over a 50 minute interval to a cold stirred mixture of n-dodecyl mercaptan (123 grams, 0.608 mole) and sodium methoxide (0.5 gram). The temperature of the reaction mixture during the resulting reaction is held at 25°–30° C. by means of an ice bath while the reaction mixture is stirred for about 16–17 hours. Thereafter, a filter aid (filtercel, 1 gram) is added and the resulting mixture is filtered through a sintered glass funnel. The filtered mixture is distilled under reduced pressure, thereby yielding methyl 3-n-dodecylthiopropionate as a high-purity liquid product.

Methyl esters of other acids of Formula C where n is 2 are similarly obtained by substantially the same procedure except substituting for n-dodecyl mercaptan an equimolar amount of such alkyl mercaptans as (a) ethyl mercaptan, (b) n-hexyl mercaptan, (c) n-octyl mercaptan, (d) n-decyl mercaptan, (e) n-tetradecyl mercaptan, (f) n-hexadecyl mercaptan, (g) n-octadecyl mercaptan and the like, thereby respectively yielding (a) methyl 3-ethylthiopropionate, (b) methyl 3-n-hexylthiopropionate, (c) methyl 3-n-octylthiopropionate, (d) methyl 3-n-decylthiopropionate, (e) methyl 3-n-tetradecylthiopropionate, (f) methyl 3-n-hexadecylthiopropionate, (g) methyl 3-n-octadecylthiopropionate and the like. The corresponding ethyl esters are obtained by substituting for methyl acrylate an equimolar amount of ethyl acrylate in such procedure.

Substitution for methyl acrylate of equimolar amounts of ethyl esters of higher alkenoic acids having from 4 to about 11 carbon atoms, e.g., ethyl 3-butenate and ethyl 4-pentenate, in combination with substitution for sodium methoxide of 2,2'-azo-bis-isobutyronitrile in a catalytically equivalent amount results in obtaining ethyl esters of acids of Formula C where n is correspondingly from 3 to about 10, e.g., ethyl 4-n-dodecylthio-n-butyrate and ethyl 5-n-dodecylthio-n-pentanoate. Additional substitution for n-dodecyl mercaptan of an equimolar amount of such alkyl mercaptans as those set forth in the above description of methyl esters of other acids of Formula C where n is 2 (e.g., ethyl mercaptan, n-octyl mercaptan and n-octadecyl mercaptan) results in yielding the corresponding ethyl alkylthioalkanates (e.g., ethyl 4-ethyl-n-butyrate, ethyl 4-n-octyl-n-butyrate and ethyl 4-n-octadecyl-n-butyrate, the corresponding ethyl 5-alkyl-pentanoates and the like).

Where n is 1, the lower alkyl esters of the acids of Formula C, e.g., methyl or ethyl 2-n-dodecylthioacetate, can be prepared for all values of k from 1 to about 30 by reacting an alpha-alkene of the formula $$(C_sH_{2s+1})-CH=CH_2$$

where s is an integer equal to k−2 and k is as defined above with thioglycolic acid, which has the formula $$HS-CH_2-\overset{O}{\underset{\|}{C}}-OH$$

generally in accordance with the method for addition of thioglycolic acid to alpha-alkenes described by Smith et al., Acta Chem. Scand. 8 (1954) No. 7, pages 1111–1119, followed by esterification of the resulting acid of the formula $$C_kH_{2k+1}-S-CH_2-\overset{O}{\underset{\|}{C}}-OH$$

where k is as defined above with a lower alkanol, e.g., methanol or ethanol. Such esterification is conducted via well known esterification procedures in the presence of an acidic catalyst such as p-toluenesulfonic acid with removal of the water formed as by distillation, thereby forming a lower alkyl ester, e.g., the methyl or ethyl ester, of an acid of Formula C.

By way of illustration, methyl 2-n-dodecylthioacetate can be prepared by reacting n-dodecene-1 as the alkene with thioglycolic acid in the method described by Smith et al. supra at page 1118, followed by esterification of the resulting 2-n-dodecylthioacetic acid with methanol. More particularly, equimolar amounts of n-dodecene-1 and thioglycolic are mixed and the resulting reaction mixture is shaken. The resulting exothermic reaction starts quickly, the mixture soon becomes substantially homogeneous and the temperature rises to about 50°-60° C. Within about one half hour the reaction temperature decreases to approximately room temperature (e.g., about 20°-30° C.). Thereafter, the reaction mixture is distilled to remove unreacted reactants, whereby n-dodecylthioacetic acid is obtained in good yield. Corresponding alkylthioacetic acids are obtained by substituting for dodecene-1 equimolar amounts of other alpha-alkenes having from 2 to about 30 carbon atoms, e.g., ethylene, propene-1, butene-1, hexene-1, octene-1, nonene-1, 4-methyldecene-1, decene-1, undecene-1, tetradecene-1, hexadecene-1, octadecene-1 and the like. The methyl esters of n-dodecylthioacetic acid and other alkylthioacetic acids are obtained by admixing the acid with a 5-15% stoichiometric excess of methanol and about 0.5 mole of p-toluenesulfonic acid per mole of the thioacid, heating the resulting reaction mixture with stirring for about 5-10 hours and distilling the reaction mixture to remove unreacted reactants and water formed during the reaction.

It is well known that upon processing polyethylenes at elevated temperature, cross-linking takes place. This results in an apparent increase in molecular weight and hence lower melt index values. More importantly, it also results in a change in molecular weight distribution by increasing, due to cross-linking, the high molecular weight tail. In many applications, it is desired that polyethylene not cross-link while being processed. Accordingly, a feature of a good stabilizer is that the melt index does not appreciably decrease when working a polyethylene as in extrusion operations.

In contrast to polyethylenes, polypropylene typically undergoes chain scission during processing thereof at elevated temperatures, i.e. a reduction in apparent molecular weight. This is reflected typically in melt flow rate values which increase as the molecular weight decreases.

EXAMPLES

Practice of the present invention is illustrated by the following non-limiting examples. All parts, percents and other amounts given throughout this disclosure, including the examples which follow, are by weight unless otherwise indicated. The percent (%) amounts shown for the various additives are the same as parts thereof per 100 parts of the organic material (e.g. polypropylene). The transesterification reactions in examples 1 and 3 to 6 were monitored by high performance liquid chromatography for the amount of the phenolic lower alkyl ester in the reaction mixtures. In each case, after 10% or less of the charged amount of such ester was detected, the pressure in the reaction vessel was increased from reduced pressure to about 760 mm Hg and cooling of the reaction mixture was begun.

EXAMPLE 1

(Compounds I to VII and Mixture EX-1)

A five-liter round bottom, 3-neck flask equipped with a stirrer, nitrogen inlet, cold trap, condenser and nitrogen outlet was purged with nitrogen. The nitrogen purged flask was charged with 802 grams (g) (2.62 moles) ethyl 3-(3,5-di-tert-butyl-4-hydroxyphenyl)propionate (EHCE), 791.24 g (2.62 moles) ethyl 3-n-dodecylthiopropionate (ETE), 55.8 g Irganox 1010 (trademark for a product consisting essentially of pentaerythritol tetrakis-ten, Ciba-Geigy Corporation, Ardsley, N.Y.), 300 g dimethylformamide (DMF), 167.9 g (1.23 moles) pentaerythritol and 8.52 g potassium tert-butoxide. The vapor space of the flask was connected to a source of vacuum and the resulting reaction mixture, which was stirred throughout the ensuing reaction, was heated for 3½ hours at 90° C. and 30 mm Hg pressure. Additional potassium tert-butoxide (1.0 g) was then added and the reaction mixture was heated for 6 hours at 135° C. After then adding another 1.0 g potassium tert-butoxide, heating was continued for 6 hours at 135°-150° C. and 15-20 mm Hg pressure. Next, the pressure was reduced to about 5 mm Hg and the temperature of the reaction mixture was increased to 175° C., which conditions were maintained for one hour. Evolved ethanol (formed during the reaction) and evolved DMF were collected in the cold trap throughout the reaction.

Thereafter, the flask was isolated from the vacuum source, the pressure was increased to about 760 mm Hg by introducing nitrogen, and the reaction mixture was cooled to room temperature (approximately 20°-25° C.). Hexane, 300 ml, was added to the cooled mixture, which was then neutralized with acetic acid and filtered. The resulting solution was extracted twice with distilled water. After drying the extracted solution over anhydrous magnesium sulfate, hexane was removed therefrom under reduced pressure. The resulting brownish yellow liquid product (hereinafter referred to as "Mixture EX-1") was analyzed by analytical high performance liquid chromatography (HPLC). The ratios (wt./wt.) of Compounds II through VII to Compound I in the product were accordingly calculated to be as follows:

| Mixture EX-1 | |
|---|---|
| Compound | Relative Ratio |
| I | 1.0 |
| II | 1.63 |
| III | 1.02 |
| IV | 0.13 |
| V | 0.32 |
| VI | 0.46 |
| VII | 0.24 |

Example 6 below describes preparation of a related mixture (Mixture EX-6) containing Compounds I through VII, albeit in amounts differing from the ratios in Mixture EX-1. Compounds I through VII were separated from Mixture EX-6 using the above-described General Separation Procedure as described in greater detail below.

Compounds I, II and III

The vertical column employed was a quartz column, 1 inch in diameter, packed with 100 g silica gel, 230-400 mesh (Kieselgel 60 EM Reagents, E. Merck, Darmstadt, West Germany) and filled with methylene chloride (MC) to slightly above the top of the packing. A solution of 10 g Mixture EX-6 in 10 ml MC was introduced and thereafter eluted with 500 ml MC. About 500 ml of a yellowish solution was collected and MC was removed therefrom under reduced pressure.

The resulting residue (found by analytical HPLC to be rich in a mixture of Compounds I, II and III) was dissolved in MC (about 10 ml) and the solution was injected into a Waters Prep 500 HPLC device equipped with a Silica Prep Pak 500 column. The injected solution was eluted with a high-pressure flow of MC at 100 ml per minute. Based on monitoring the refractive index of the elution, six fractions were collected. Each collected fraction was rich in a different one of Compounds I, II and III as determined by HPLC analyses of the fractions. The foregoing preparative HPLC procedure was repeated four times and the resulting various fractions were combined to yield three separate fractions, each rich in a different one of these compounds.

Each of these three fractions was then separately injected into the Prep 500 HPLC device to separately obtain a corresponding ultimate fraction of higher assay for its respective compound. After removing the MC from each ultimate fraction under reduced pressure, each resulting residue was analyzed by $^1$H NMR, $^{13}$C NMR and analytical HPLC. Assays for Compounds I, II and III were found to be at least 97%, 94% and 94%, respectively, in these three residues.

Compounds IV, V, VI and VII

These compounds were eluted as a group from the silica gel in the quartz column by replacing MC with ethyl acetate (EA) as the eluting liquid. A solution containing a total of about 33 g of these compounds in EA was collected. The column packing was replaced with a fresh supply of like silica gel and portions of the collected solution were chromatographed and eluted with about 2000 ml of a mixture of 99% MC and 1% acetonitrile (AN). An eluted first fraction identified by analytical HPLC as containing a mixture of Compounds IV, V and VI was collected. The column was then eluted with about 1000 ml of a mixture of 70% MC and 30% AN. A second fraction identified by analytical HPLC as containing a solution of Compound VII was collected. Solvent was removed from this fraction under reduced pressure to yield a residue rich in Compound VII.

Four portions, about 6.0 g each, of the first fraction (containing a mixture of Compounds IV, V and VI) were injected separately into the preparative HPLC device and eluted separately with a high-pressure flow of solvent (a mixture of 98% MC and 2% AN). The eluted fractions, separately rich in Compounds IV, V and VI, were collected. Each of these fractions was separately injected into the preparative HPLC device and chromatographed to yield a corresponding ultimate fraction. Solvent was removed from each ultimate fraction and the three resulting residues were analyzed by $^1$H NMR, $^{13}$C NMR and analytical HPLC. The resulting assays were at least 90% Compound IV, 95% Compound V and 93% Compound VI in the corresponding residues.

The residue rich in Compound VII was injected into the preparative HPLC device and eluted with a high-pressure flow of a solvent mixture containing 90% MC and 10% AN. After removing solvent from the eluted solution, the resulting residue was analyzed by $^1$H NMR, $^{13}$C NMR and analytical HPLC (assay: at least 75% Compound VII).

Performance Test Procedure

Each compound was separately admixed, as an additive, with polypropylene resin (Profax 6501, 3.0 nominal melt flow rate, Himont USA, Inc., Wilmington, Del.) and calcium stearate (RSN 248D, Mallinckrodt, Inc., St. Louis, Mo.). To 700 g of the unstabilized resin was added 0.7 g calcium stearate and 0.7 g Compound I. Similarly, blends separately containing Compounds II through VII and Mixture EX-1 were prepared. A blend containing calcium stearate as the only added material was also prepared.

Each blend was extruded twice in a ¾ inch Brabender extruder Model 252 (L:D ratio of 25:1) operated with its three heating zones and die at a temperature of 170° C. The extruder speed was set at 50 rpm. Each extruded rod was pelletized prior to reextrusion. Following the two compounding passes at 170° C., each blend was test extruded four times with the zones and die at 260° C. and a speed of 50 rpm, each extruded rod being water quenched and pelletized prior to reextrusion. Melt flow rate was determined in accordance with ASTM D1238-79 condition L (230° C., 2160 g) for a sample of each blend taken after each of the 260° C. extrusions. Unprocessed resin was found to have a melt flow rate of 3.6.

Samples from the second 170° C. extrusion were compression molded into plaques 25 mils in thickness and cut into strips ⅜ inch×5 inch. The strips were placed in holders in a 150° C. air circulating oven. Time to degradation was determined for these strips. As is well known to those skilled in the art, the "time to degradation" in such oven aging test is the time at which substantially the entire test piece becomes discolored and brittle.

The results are shown in Table I, which also shows results for non-stabilized polypropylene resin and for polypropylene resin containing heretofore proposed mixtures of additives in various relative amounts. These resins were prepared in accordace with the above procedure using either no additive (Comparative A) or the additives shown in Table I for Comparaives B, C and D in the amounts indicated in the table.

TABLE I

| Additive 0.1% | Melt Flow Rate, g/10 min ASTM D1238-79 Condition L | | | | Time to Degradation (Hours) |
| --- | --- | --- | --- | --- | --- |
| | 1st Extrusion at 260° C. | 2nd Extrusion at 260° C. | 3rd Extrusion at 260° C. | 4th Extrusion at 260° C. | |
| None (Comparative A) | 13.1 | 21.6 | 28.2 | — | 24 |
| 0.067% Irganox 1010[a] + 0.033% Seenox 412S[b] (Comparative B) | 3.9 | 5.9 | 8.0 | 10.2 | 840 |
| 0.05% Irganox 1010[a] + 0.05% | 4.6 | 6.1 | 9.3 | 11.5 | 528 |

TABLE I-continued

| Additive 0.1% | Melt Flow Rate, g/10 min ASTM D1238-79 Condition L | | | | Time to Degradation (Hours) |
|---|---|---|---|---|---|
| | 1st Extrusion at 260° C. | 2nd Extrusion at 260° C. | 3rd Extrusion at 260° C. | 4th Extrusion at 260° C. | |
| Seenox 412S[b] (Comparative C) | | | | | |
| 0.033% Irganox 1010[a] + 0.067% Seenox 412S[b] (Comparative D) | 5.9 | 9.4 | 13.5 | 17.3 | 432 |
| Compound I | 3.4 | 4.7 | 6.3 | 8.0 | 840 |
| Compound II | 3.8 | 5.1 | 6.6 | 9.7 | 840 |
| Compound III | 3.8 | 6.0 | 7.4 | 11.3 | 240 |
| Compound IV | 4.2 | 6.7 | 9.7 | 12.8 | 552 |
| Compound V | 4.8 | 7.5 | 10.9 | 15.1 | 528 |
| Compound VI | 5.4 | 8.4 | 11.3 | 15.5 | 336 |
| Compound VII | 4.7 | 6.9 | 10.2 | 12.2 | 240 |
| Mixture EX-1 | 3.2 | 4.8 | 6.4 | 9.2 | 984 |

[a]Trademark for a product consisting principally of pentaerythritol tetrakis[3-(3,5-di-t-butyl-4-hydroxyphenyl)propionate] (available from Ciba-Geigy Corporation, Ardsley, New York)
[b]Trademark for a product consisting principally of pentaerythritol tetrakis(3-n-dodecylthiopropionate) (available from Argus Chemical Division of Witco Chemical Corporation, Brooklyn, New York).

Example 2

In this example Mixture EX-1 (prepared in Example 1) was tested as a stabilizer for Kraton D-1107 (trademark for a styrene-isoprene-styrene block copolymer which is a thermoplastic elastomer, available from Shell Chemical Company, Houston, Tex.).

The performance test procedure of Example 1 was repeated except that 500 grams of Kraton D-1107 was substituted for the 700 grams of polypropylene, calcium stearate was omitted and 5 grams of the additive being tested was substituted for the 0.7 gram of additive used in the general procedure of Example 1. Comparative compositions were also tested.

The samples were placed on aluminum trays which were inserted into a 150° C. air circulating oven and kept there for 60 minutes. Portions, 7.5 g, from each sample were then placed in a 190° C. plastometer. After 10 minutes at 190° C., the melt flow rate values were determined using 2160 g weight (ASTM D-1238 condition E).

The following results were obtained:

| Additives | Kraton D-1107 Melt Flow Rate, g/10 min ASTM D1238 Condition E |
|---|---|
| None | 18.9 |
| Irganox 1010* (1.0%) | 9.1 |
| Seenox 412S* (1.0%) | 9.6 |
| Irganox 1010 (0.5%) plus Seenox 412S (0.5%) | 5.9 |
| Present Invention, Mixture EX-1 (1.0%) | 4.3 |

*See Table I

The results show that the mixture of the present invention is much more effective than the other additives in protecting the styrene-isoprene-styrene block copolymer against thermal degradation.

Additional mixtures of this invention were prepared in Examples 3–6.

Example 3

(Mixture EX-3)

A one-liter round bottom, 3-neck flask equipped with a stirrer, nitrogen inlet, Dean Stark apparatus, condenser and nitrogen outlet was purged with nitrogen. The nitrogen purged flask was charged with 228.4 g (0.782 mole) methyl 3-(3,5-di-tert-butyl-4-hydroxyphenyl)propionate [MHCE], 226.4 g (0.786 mole) methyl 3-n-dodecylthiopropionate [MTE], 16.74 g Irganox 1010 (Ciba-Geigy Corporation, Ardsley, N.Y.), 52.38 g (0.385 mole) pentaerythritol and 2.6 g potassium tert-butoxide. Although no inert solvent was employed in the reaction of this example, the resulting reaction mixture was liquid and readily stirrable. The reaction mixture, which was stirred throughout the ensuing reaction, was heated for 5 hours at about 760 m Hg under a moderately strong flow of nitrogen, such that the temperature of the mixture was gradually increased to about 135° C. during the 5 hour period. Methanol formed by the reaction was removed by the flow and collected in the Dean Stark apparatus. After collecting about 60–70% of the theoretical amount of methanol, 2 g of sodium methoxide was added and the Dean Stark apparatus was replaced with a cold trap. The flask pressure was then reduced to about 10–20 mm Hg by connecting the vapor space of the flask through the cold trap to a source of vacuum and the temperature of the reaction mixture was increased to 145° C. Heating at 145° C. and this reduced pressure was continued for about 6 hours, during which time additionally formed methanol was collected and trapped in the cold trap, which was cooled by an acetone-dry ice bath.

The resulting reaction product was recovered as next described. The reaction mixture was restored to atmospheric pressure (about 760 mm Hg) by introducing nitrogen and cooled to room temperature (about 20°–25° C.). Hexane, 300 ml, was added to the cooled mixture, which was then neutralized with acetic acid and filtered. The resulting solution was extracted twice with distilled water. After drying the extracted solution over anhydrous magnesium sulfate, hexane was removed under reduced pressure and the resulting brownish yellow liquid product (hereinafter referred to as "Mixture EX-3") was analyzed by analytical high performance liquid chromatography (HPLC). The ratios (wt./wt.) of Compounds II through VII to Compound I in the product were accordingly calculated to be as follows:

| Mixture EX-3 | |
| --- | --- |
| Compound | Relative Ratio |
| I | 1.0 |
| II | 1.08 |
| III | 0.14 |
| IV | 0.20 |
| V | 0.45 |
| VI | 0.74 |
| VII | 0 |

Example 4

(Mixture EX-4)

A one-liter round bottom, 3-neck flask equipped as described in Example 3 was purged with nitrogen. The nitrogen purged flask was charged with 381 g (1.30 moles) MHCE, 375 g (1.30 moles) MTE, 87.3 g dimethylformamide (DMF), 42 g Irganox 1010, 0.28 g hydroquinone, 87.3 g (0.64 mole) pentaerythritol and 5 g potassium tert-butoxide. The temperature of the resulting reaction mixture, which was stirred throughout the ensuing reaction, was gradually increased to about 140°–145° (over a period of 2 hours), while methanol formed by the reaction was removed by a continuous, moderately strong flow of nitrogen at a pressure of about 760 mm Hg. Such flow and temperature were maintained thereafter for about 4 hours, during which time additionally formed methanol was removed by the flow of nitrogen. Removed methanol was collected in the Dean Stark apparatus. Next, sodium methoxide (5 g) was added, and the flask pressure was reduced to about 20–25 mm Hg by connecting the vapor space of the flask via a cold trap to a source of vacuum. Reaction under these conditions was continued for about 3 hours, during which time additionally formed methanol was collected in the trap, which was cooled by an acetone-dry ice bath. The resulting product was recovered using the recovery procedure described in Example 3. The recovered light yellow product (hereinafter referred to as "Mixture EX-4") was analyzed by analytical HPLC, whereby the ratios (wt./wt.) of Compounds II through VII in the product were calculated to be as follows:

| Mixture EX-4 | |
| --- | --- |
| Compound | Relative Ratio |
| I | 1.0 |
| II | 1.04 |
| III | 0.46 |
| IV | 0.11 |
| V | 0.20 |
| VI | 0.28 |
| VII | 0 |

EXAMPLE 5

(Mixture EX-5)

A 500-ml round bottom, 3-neck flask equipped and purged as described in Example 3 was charged with 79.7 g (0.26 mole) of ethyl 3-(3,5-di-tert-butyl-4-hydroxyphenyl)propionate [EHCE], 79.15 g (0.26 mole) ethyl 3-n-dodecylthiopropionate [ETE], 2.79 g Irganox 1010, 22.3 g (0.164 mole) pentaerythritol and 0.90 g potassium tert-butoxide. Reaction in the resulting reaction mixture and recovery and analysis of the resulting reaction product were carried out substantially according to the procedure of Example 4 except as follows: at the end of the initial period of heating to about 140°–145° C., the following approximately 4-hour period of maintaining the nitrogen flow and such temperature was reduced to 2 hours; potassium tert-butoxide (0.9 g) was added at the end of the initial period in lieu of the subsequent addition of sodium methoxide employed in Example 4; reaction was continued under reduced pressure for one hour in lieu of the approximately 3-hour period employed in Example 4; and, in lieu of methanol, ethanol was formed, removed and collected. The recovered product (hereinafter referred to as Mixture EX-5) was found to have the following ratios (wt./wt.) of Compounds II through VII to Compound I:

| Mixture EX-5 | |
| --- | --- |
| Compound | Relative Ratio |
| I | 1.0 |
| II | 1.24 |
| III | 0.77 |
| IV | 0.66 |
| V | 1.52 |
| VI | 2.54 |
| VII | 1.08 |

Example 6

(Mixture EX-6)

A 500-ml round bottom, 3-neck flask equipped and purged as described in Example 3 was charged with 79.7 g (0.26 mole) EHCE, 79.15 g (0.26 mole) ETE, 5.58 g Irganox 1010, 39.5 g (0.29 mole) pentaerythritol and 0.85 g potassium tert-butoxide. Reaction in the resulting reaction mixture and recovery and analysis of the resulting reaction product were carried out substantially according to the procedure of Example 4 except as follows: at the end of the initial period of heating to about 140°–145° C. (which period was 2 hours in this example), the following approximately 4-hour period of maintaining the nitrogen flow and such temperature was reduced to a 2-hour period (by the end of which time the rate of ethanol removal had slowed considerably); the addition of sodium methoxide employed in Example 4 was omitted; reaction was continued under reduced pressure for 40 minutes in lieu of the approximately 3-hour period employed in Example 4; and as indicated above, in lieu of methanol, ethanol was formed, removed and collected. The recovered product (hereinafter referred to as Mixture EX-6) was found to have the following ratios (wt./wt.) of Compounds II through VII to Compound I:

| Mixture EX-6 | |
| --- | --- |
| Compound | Relative Ratio |
| I | 1.0 |
| II | 1.19 |
| III | 0.53 |
| IV | 2.14 |
| V | 2.90 |
| VI | 5.12 |
| VII | 0.90 |

Example 7

(Additional Tests in Polypropylene)

Blends of polypropylene (100 parts) each containing calcium stearate (0.1 part) and, as the additive being tested, one of Mixtures EX-3 through EX-6 (0.1 part)

were prepared and tested in accordance with the Performance Test Procedure of Example 1. The blends were evaluated for change in melt flow rate on repeated extrusion and for long term oven stability in air at 150° C. The following results were obtained:

| Mixture | Melt Flow Rate, g/10 min ASTM D1238 Condition L | | | | Time to Degradation (Hours) |
|---|---|---|---|---|---|
| | 1st Extrusion at 260° C. | 2nd Extrusion at 260° C. | 3rd Extrusion at 260° C. | 4th Extrustion 260° C. | |
| None | 13.1 | 21.6 | 28.2 | — | 24 |
| EX-3 | 3.2 | 4.8 | 6.8 | 8.5 | 912 |
| EX-4 | — | — | — | — | 936 |
| EX-5 | 4.0 | 6.2 | 8.7 | 11.7 | 768 |
| EX-6 | 4.7 | 6.8 | 9.1 | 12.0 | 408 |

Example 8

(Tests in LLDPE of Mixture EX-1)

Unstabilized linear low density polyethylene (LLDPE) resin used in this example is the precursor to Union Carbide G-resin 7047 Natural 7 antioxidant-modified product. The resin, which contains units of ethylene (97–95 mole %) and 1-butene (3–5 mole %) as a comonomer, typically has a density of about 0.92 and a melt index of about 1.0 (ASTM D1238-79 condition E).

The LLDPE resin (1000 g) was dry blended with 1 g Mixture EX-1 as an additive. The resulting blend composition was extruded in accordance with the extrusion portion of the Performance Test Procedure set forth in Example 1 except that the two compounding passes were performed at 160° C. and five test extrusions were employed.

The melt index of each of the pelletized compositions resulting from the first, third and fifth extrusions at 260° C. was determined according to ASTM D1238-79 condition E (190° C., 2160 g).

Samples from the second compounding extrusion at 160° C. were compression molded at 170° C. and 10 tons pressure into plaques 25 mils in thickness. Twelve chips, each about 1 inch in diameter were cut from each plaque and inserted into a 150° C. air circulating oven. Time to degradation was determined for these chips.

The results of the measurements of melt index and time to degradation are shown below. Also shown are results for a control, i.e., a composition consisting of 1000 g LLDPE processed as described above but without any added additive, and an identically prepared and tested composition except that Mixture EX-1 was replaced by a like amount of Irganox 1010.

| Additive | Melt Index, g/10 min. ASTM D1238 Condition E | | | Hours to Degradation at 150° C. |
|---|---|---|---|---|
| | 1st Extrusion at 260° C. | 3rd Extrusion at 260° C. | 5th Extrusion at 260° C. | |
| None | 0.61 | 0.38 | 0.29 | 24 |
| Mixture EX-1 | 1.06 | 1.01 | 0.89 | 576 |
| Irganox 1010* | 1.06 | 0.98 | 0.93 | 432 |

*See Table I

Example 9

(Performance in Thermoplastic Elastomers)

Kraton D-1102 and Kraton D-1107 are trademarks for thermoplastic elastomers commercially available from Shell Chemical Company. Kraton D-1102 is a styrene-butadiene-styrene (SBS) block copolymer with a styrene:diene ratio of 28:72. It generally crosslinks on exposure to heat. Kraton D-1107 is a styrene-isoprene-styrene (SIS) block copolymer with a styrene:diene ratio of 14:86. It generally undergoes chain scission on exposure to heat.

Mixtures of this invention which are identified below were incorporated, as additives, into 50-gram portions of each of the thermoplastic elastomers. The resulting elastomeric compositions were tested for resistance to degradation as more particularly described below. The additive (0.25 g, 0.50 g or 1.0 g) was dissolved in 25 ml methanol contained in a 50 ml beaker. The thermoplastic elastomer, 50 g, was added to 150 ml methanol in a 500 ml round bottom flask. The methanol solution of the additive was added to the resulting methanol-elastomer mixture. The beaker was washed with additional methanol and the washings were added to the methanol-elastomer mixture. The total amount of methanol in the flask was about 300 ml. After stirring the resulting mixture for about 10 minutes at 50° C., most of the methanol was removed via rotary evaporation. The resulting methanol-wet elastomer-additive blend was transferred to a beaker and inserted into a vacuum oven for drying, which was continued for 24 hours. One-third portions of the resulting dried elastomer-additive blend were transferred to three aluminum trays, which were then inserted into a 150° C. air circulating oven. The trays were removed after periods of 15, 30 and 60 minutes. Melt flow rate values for a 7.5-gram blend sample from each tray were then determined according to ASTEM D1238-79 condition E (190° C., 2160 g).

In an identical manner, samples of Kraton D-1102 and D-1107 to which no additive was added were prepared and evaluated for heat stability.

The following results were obtained:

Kraton TM D-1102 SBS Block Copolymer

| Additive | Melt Flow Rate, g/10 min ASTM D1238 Condition E Time in Oven at 150° C. | | |
|---|---|---|---|
| | 15 min | 30 min | 60 min |
| None | 3.0 | 2.4 | 2.0 |
| Mixture EX-5, 1.0% | 3.7 | 3.8 | 3.9 |
| Mixture EX-1, 1.0% | 3.9 | 3.9 | 4.1 |

Kraton ™ D-1107 SIS Block Copolymer

| Additive | Melt Flow Rate, g/10 min ASTM D1238 Condition E Time in Oven at 150° C. | | |
|---|---|---|---|
| | 15 min | 30 min | 60 min |
| None | 2.7 | 7.2 | 22.2 |
| Mixture EX-4, 1.0% | — | 2.4 | 4.0 |
| Mixture EX-5, 1.0% | 2.6 | 2.8 | 4.4 |
| Mixture EX-1, 0.5% | 2.3 | 3.0 | 7.5 |
| Mixture EX-1, 1.0% | — | — | 4.3 |
| Mixture EX-1, 2.0% | 2.3 | 2.4 | 3.0 |

Example 10

(Mixture EX-6A)

A portion of Mixture EX-6 was placed on a preparative HPLC silica column. After eluting compound I, II and III, the column was treated with methanol and compounds IV, V, VI and VII were obtained as a mixture (hereinafter referred to as "Mixture 6-A") having the following relative composition:

| Mixture EX-6A | |
|---|---|
| Compound | Relative Ratio |
| IV | 1.0 |
| V | 2.23 |
| VI | 4.45 |
| VII | 1.50 |

Performance for this mixture in polypropylene was evaluated in accordance with the Performance Test Procedure of Example 1. The results appear below:

| Additive | Melt Flow Rate, g/10 min. ASTM D1238 Condition L | | | | Time to Degradation (Hours) |
|---|---|---|---|---|---|
| | 1st Extrusion at 260° C. | 2nd Extrusion at 260° C. | 3rd Extrusion at 260° C. | 4th Extrusion at 260° C. | |
| Mixture EX-6A | 4.1 | 5.3 | 7.0 | 9.5 | 408 |

Mixture EX-4 is contemplated to be the most commercially attractive stabilizer of this invention. Example 4 sets forth the best mode contemplated for making such mixture, it being contemplated that large-scale quantities could best be made using an apparatus and process which are scaled-up in accordance with industrially accepted scale-up practices.

BEST MODE CONTEMPLATED

The best mode contemplated for carrying out this invention has been set forth in the above description, for example, by way of setting forth preferred materials and operating conditions, including but not limited to preferred ranges and values of amounts and other nonobvious variables material to successfully practicing the invention in the best way contemplated at the time of executing this patent application.

It is understood that the foregoing detail description is given merely by way of illustration and that many modifications may be made therein without departing from the spirit or scope of the present invention.

What is claimed is:

1. A method for making the compound of the formula:

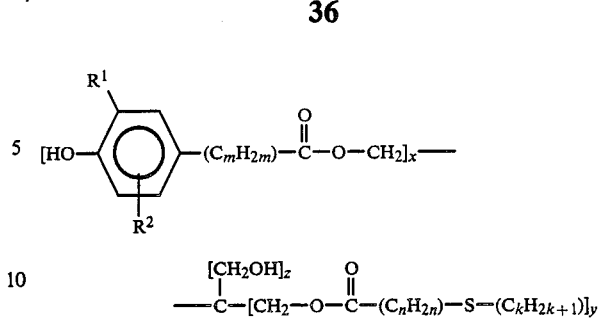

wherein

R$^1$ is methyl, ethyl, an alpha-branched acyclic alkyl group having from 3 to 10 carbon atoms, or a cycloalkyl group having from 5 to 12 carbon atoms;

R$^2$ is hydrogen, methyl, ethyl, an alpha-branched acyclic alkyl group having from 3 to 10 carbon atoms, or a cycloalkyl group having from 5 to 12 carbon atoms and R$^2$ is meta or para to R$^1$;

n is an integer from 1 to about 10;

k is an integer from 1 to about 30;

x is 1, 2 or 3;

y is 1, 2 or 3; and z is zero, 1 or 2;

subject to the provisos that (a) the sum of x, y and z is 4;

(b) when z is zero, y is 1, 2 or 3 and x is 4-y;

(c) when z is 2, each of x and y is 1;

(d) when x is 2 or 3, each R$^1$ is selected independently of each other R$^1$, each R$^2$ is selected independently of each other R$^2$ and each m is selected independently of each other m; and (e) when y is 2 or 3, each n is selected independently of each other n and each k is selected independently of each other k comprising esterification of pentaerythritol by reacting it with (a) at least one mono- or dialkyl -4-hydroxyphenylalkanoic acid having the formula

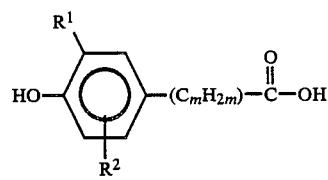

wherein R$^1$, R$^2$ and m are as defined above and (b) at least one member selected from the group consisting of alkylthioalkanoic acids, acid chlorides thereof, and lower alkyl esters thereof wherein said alkylthioalkanoic acids have the formula

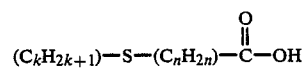

wherein k and n are as defined above.

2. The method of claim 1 wherein the esterification is conducted in the presence of an acid catalyst.

3. The method of claim 1 wherein the esterification is conducted in the presence of an acid scavenger which serves as the reaction medium.

4. The method of claim 3 wherein a solvent is also present to improve solubility of the reactants.

5. The method of claim 1 wherein the esterification is conducted in the presence of a transesterification catalyst selected from the group consisting of alkali metal hydrides, alkali metal alkoxides and mixtures thereof.

6. The method of claim 5 wherein the catalyst is sodium methoxide.

7. The method of claim 5 wherein the catalyst is potassium tert-butoxide.

8. The method of claim 5 wherein the catalyst is present in an amount of from about 0.01 to about 0.03 mole equivalent per mole of pentaerythritol.

9. The method of claim 5 wherein the esterification is carried out in an inert solvent.

10. The method of claim 9 wherein the solvent is dimethyl formamide.

11. The method of claim 1 wherein the reaction is conducted at from about 80 to about 220 degrees centigrade and at a pressure of from about 0.1 to about 760 millimeters of mercury.

12. The method of claim 5 wherein the esterification is conducted in two phases comprising
(a) an initial phase under an inert gaseous blanket comprising removing lower alkanols which form during the transesterification after about three to five hours of reaction and thereafter,
(b) a second phase wherein the reaction mixture is stirred under reduced pressure for the purpose of removing solvent and lower alkanols and increasing the amount of desired product, said reduced pressure being about 50 millimeters mercury absolute or less the time period being from about three to about eight hours.

13. The method of claim 1 wherein the ratio of mono- or dialkyl -4-hydroxyphenyl-alkanoic acids to alkylthioalkanoic acids, acid chlorides thereof, or lower alkylesters thereof in the reaction mixture is from about 0.8:1 to about 1.2:1.

* * * * *

UNITED STATES PATENT AND TRADEMARK OFFICE
CERTIFICATE OF CORRECTION

PATENT NO. : 4,806,675

DATED : February 21, 1989

INVENTOR(S) : N. Dunski and A. Bazzi

It is certified that error appears in the above-identified patent and that said Letters Patent is hereby corrected as shown below:

Column 34, line 53, "ASTEM D1238-79" should be --- ASTM D1238-79 ---

Column 36, line 21, Claim 1, before "$n$ is an integer from 1 to about 10;" please add --- $m$ is an integer from 1 to about 6; ---.

Signed and Sealed this

Seventeenth Day of April, 1990

*Attest:*

HARRY F. MANBECK, JR.

*Attesting Officer*   *Commissioner of Patents and Trademarks*